US010624746B2

(12) United States Patent
Jones et al.

(10) Patent No.: US 10,624,746 B2
(45) Date of Patent: Apr. 21, 2020

(54) FLUID INTERFACE SYSTEM FOR IMPLANTS

(71) Applicant: HD LifeSciences LLC, Woburn, MA (US)

(72) Inventors: Christopher L. Jones, Malden, MA (US); Ian Helmar, Beverly, MA (US); Lucas Diehl, Beverly, MA (US); Jason Tinley, Fort Worth, TX (US); Kevin D. Chappuis, Malden, MA (US); John F. Sullivan, Pelham, NH (US)

(73) Assignee: HD LifeSciences LLC, Woburn, MA (US)

( * ) Notice: Subject to any disclaimer, the term of this patent is extended or adjusted under 35 U.S.C. 154(b) by 0 days.

(21) Appl. No.: 15/941,193

(22) Filed: Mar. 30, 2018

(65) Prior Publication Data

US 2018/0280139 A1 Oct. 4, 2018

Related U.S. Application Data

(60) Provisional application No. 62/480,383, filed on Apr. 1, 2017, provisional application No. 62/480,388, filed
(Continued)

(51) Int. Cl.
*A61F 2/28* (2006.01)
*A61F 2/44* (2006.01)
(Continued)

(52) U.S. Cl.
CPC ............ *A61F 2/28* (2013.01); *A61F 2/30767* (2013.01); *A61F 2/4455* (2013.01); *A61F 2/44* (2013.01);
(Continued)

(58) Field of Classification Search
CPC ....... A61F 2/28; A61F 2/4455; A61F 2/30767
See application file for complete search history.

(56) References Cited

U.S. PATENT DOCUMENTS

| 5,615,528 A | 4/1997 | Owens |
| 5,674,294 A | 10/1997 | Bainville et al. |

(Continued)

FOREIGN PATENT DOCUMENTS

| CN | 204971711 U | 1/2016 |
| WO | 1999033641 A1 | 7/1999 |

(Continued)

OTHER PUBLICATIONS

Ahmadi, S. et al., "Additively Manufactured Open-Cell Porous Biomaterials Made from Six Different Space-Filling Unit Cells: The Mechanical and Morphological Properties," Materials, vol. 8:1871-1896 (2015).

(Continued)

*Primary Examiner* — Jason-Dennis N Stewart
(74) *Attorney, Agent, or Firm* — Nelson Mullins Riley & Scarborough LLP; Thomas J. Engellenner; Reza Mollaaghababa

(57) ABSTRACT

The present invention includes a fluid interface system for use in medical implants. The fluid interface system of the present invention can include one or more fluid interface channels disposed within an implant. The fluid interface systems can optionally include fluid redirection channels, fluid interface ports and a corresponding instrument to transfer fluid in or out of the fluid interface ports.

20 Claims, 19 Drawing Sheets

Related U.S. Application Data on Apr. 1, 2017, provisional application No. 62/480,393, filed on Apr. 1, 2017, provisional application No. 62/619,260, filed on Jan. 19, 2018.

(51) Int. Cl.
  *A61F 2/30* (2006.01)
  *A61L 27/04* (2006.01)
(52) U.S. Cl.
  CPC .............. *A61F 2002/30006* (2013.01); *A61F 2002/30011* (2013.01); *A61F 2002/3028* (2013.01); *A61F 2002/30062* (2013.01); *A61F 2002/3092* (2013.01); *A61F 2002/30586* (2013.01); *A61F 2002/30784* (2013.01); *A61L 27/045* (2013.01)

(56) References Cited

U.S. PATENT DOCUMENTS

| | | |
|---|---|---|
| 6,206,924 B1 | 3/2001 | Timm |
| 7,637,950 B2 | 12/2009 | Baccelli et al. |
| D619,255 S | 7/2010 | Richter et al. |
| D626,233 S | 10/2010 | Cipoletti et al. |
| 7,850,731 B2 | 12/2010 | Brittan et al. |
| D653,757 S | 2/2012 | Binder |
| D682,427 S | 5/2013 | Farris et al. |
| D692,136 S | 10/2013 | Tyber |
| 8,697,231 B2 | 4/2014 | Longepied et al. |
| 8,740,983 B1 | 6/2014 | Arnold et al. |
| D708,747 S | 7/2014 | Curran et al. |
| D711,537 S | 8/2014 | Pimenta et al. |
| D737,446 S | 8/2015 | Butler et al. |
| D750,249 S | 2/2016 | Grimberg, Jr. et al. |
| 9,308,076 B2 | 4/2016 | Ringeisen et al. |
| 9,456,901 B2 | 10/2016 | Jones et al. |
| D789,539 S | 6/2017 | Kleiner et al. |
| D816,844 S | 5/2018 | Ricca et al. |
| 9,962,269 B2 | 5/2018 | Jones et al. |
| D833,012 S | 11/2018 | Jones et al. |
| D833,611 S | 11/2018 | Jones et al. |
| D833,612 S | 11/2018 | Jones et al. |
| D835,279 S | 12/2018 | Jones et al. |
| D835,788 S | 12/2018 | Jones et al. |
| D840,036 S | 2/2019 | Jones et al. |
| 10,368,997 B2 | 8/2019 | Jones et al. |
| 10,405,983 B2 | 9/2019 | Jones et al. |
| 2003/0114936 A1* | 6/2003 | Sherwood .............. A61F 2/28 623/23.58 |
| 2004/0258732 A1 | 12/2004 | Shikinami |
| 2005/0049706 A1 | 3/2005 | Brodke et al. |
| 2005/0129726 A1 | 6/2005 | Liebschner |
| 2005/0251083 A1 | 11/2005 | Carr-Brendel et al. |
| 2006/0147332 A1 | 7/2006 | Jones et al. |
| 2006/0259144 A1 | 11/2006 | Trieu |
| 2006/0276925 A1 | 12/2006 | Lin et al. |
| 2007/0142914 A1 | 6/2007 | Jones et al. |
| 2008/0161927 A1 | 7/2008 | Savage et al. |
| 2008/0169585 A1 | 7/2008 | Zinniel |
| 2008/0269903 A1 | 10/2008 | Francis et al. |
| 2008/0306596 A1 | 12/2008 | Jones et al. |
| 2008/0306609 A1 | 12/2008 | Lee et al. |
| 2009/0037148 A1 | 2/2009 | Lin et al. |
| 2009/0182429 A1 | 7/2009 | Humphreys et al. |
| 2009/0317278 A1 | 12/2009 | Kokubo |
| 2010/0087925 A1 | 4/2010 | Kostuik et al. |
| 2010/0100185 A1* | 4/2010 | Trieu .................... A61F 2/4425 623/17.16 |
| 2010/0145459 A1 | 6/2010 | McDonough et al. |
| 2011/0004307 A1 | 1/2011 | Ahn et al. |
| 2011/0029084 A1 | 2/2011 | Milbocker et al. |
| 2011/0029087 A1 | 2/2011 | Haider et al. |
| 2011/0144764 A1 | 6/2011 | Bagga et al. |
| 2012/0022653 A1 | 1/2012 | Kirschman |
| 2012/0150299 A1 | 6/2012 | Ergun et al. |
| 2012/0177939 A1 | 7/2012 | Longepied et al. |
| 2012/0179258 A1 | 7/2012 | Glazer et al. |
| 2012/0215310 A1 | 8/2012 | Sharp et al. |
| 2012/0303128 A1 | 11/2012 | Ullrich, Jr. et al. |
| 2012/0321878 A1 | 12/2012 | Landon et al. |
| 2013/0218276 A1 | 8/2013 | Fiechter et al. |
| 2013/0325129 A1 | 12/2013 | Huang |
| 2014/0107786 A1 | 4/2014 | Geisler et al. |
| 2014/0121776 A1 | 5/2014 | Hunt |
| 2014/0277482 A1 | 9/2014 | Gfeller et al. |
| 2015/0005885 A1 | 1/2015 | Zhang et al. |
| 2015/0025635 A1 | 1/2015 | Laubert |
| 2015/0100126 A1 | 4/2015 | Melkent et al. |
| 2015/0360421 A1 | 12/2015 | Burhop et al. |
| 2016/0022431 A1 | 1/2016 | Wickham |
| 2016/0027425 A1 | 1/2016 | Cook et al. |
| 2016/0038301 A1 | 2/2016 | Wickham |
| 2016/0085882 A1 | 3/2016 | Li et al. |
| 2016/0113775 A1 | 4/2016 | Willis et al. |
| 2016/0184103 A1 | 6/2016 | Fonte et al. |
| 2016/0199193 A1 | 7/2016 | Willis et al. |
| 2017/0014235 A1 | 1/2017 | Jones et al. |
| 2017/0095337 A1 | 4/2017 | Pasini et al. |
| 2017/0348114 A1 | 12/2017 | Jones et al. |
| 2018/0140427 A1 | 5/2018 | Conway et al. |
| 2018/0221156 A1 | 8/2018 | Jones et al. |
| 2018/0228570 A1 | 8/2018 | Jones et al. |
| 2018/0228612 A1 | 8/2018 | Jones et al. |
| 2018/0228613 A1 | 8/2018 | Jones et al. |
| 2018/0243094 A1 | 8/2018 | Jones et al. |
| 2018/0243097 A1 | 8/2018 | Jones et al. |
| 2018/0280139 A1 | 10/2018 | Jones et al. |
| 2018/0280140 A1 | 10/2018 | Jones et al. |
| 2018/0280141 A1 | 10/2018 | Jones et al. |
| 2018/0280144 A1 | 10/2018 | Jones et al. |
| 2018/0280145 A1 | 10/2018 | Jones et al. |
| 2019/0150910 A1 | 5/2019 | Jones et al. |

FOREIGN PATENT DOCUMENTS

| | | |
|---|---|---|
| WO | 2015164982 A1 | 11/2015 |
| WO | 2016061148 A1 | 4/2016 |
| WO | 2017/214114 A1 | 12/2017 |
| WO | 2018/152077 A1 | 8/2018 |
| WO | 2018/156905 A1 | 8/2018 |
| WO | 2018/182834 A1 | 10/2018 |
| WO | 2018/183809 A1 | 10/2018 |

OTHER PUBLICATIONS

Babaee S., et al., "Mechanical properties of open-cell rhombic dodecahedron cellular structures," Acta Materialia, vol. 60:2873-2885 (2012).

Hoffmann, W. et al , "Rapid prototyped porous nickel-titanium scaffolds as bone substitutes," Journal of Tissue Engineering, vol. 5:1-14 (2014).

International Preliminary Report on Patentability, PCT/US2017/36111, dated Jun. 27, 2018, 26 pages.

International Preliminary Report on Patentability, PCT/US2018/017919, dated Aug. 20, 2019, 11 pages.

International Preliminary Report on Patentability, PCT/US2018/019437, dated Aug. 27, 2019, 16 pages.

International Search Report and Written Opinion, PCT/US2017/36111, dated Nov. 6, 2017, 10 pages.

International Search Report and Written Opinion, PCT/US2018/014720, dated Jun. 1, 2018, 13 pages.

International Search Report and Written Opinion, PCT/US2018/017919, dated Jun. 6, 2018, 14 pages.

International Search Report and Written Opinion, PCT/US2018/019437, dated Jun. 28, 2018, 19 pages.

International Search Report and Written Opinion, PCT/US2018/025351, dated Jun. 8, 2018, 14 pages.

Nouri, A., "Titanium foam scaffolds for dental applications," Metallic Foam Bone, Chapter 5: 130-160 (2017).

(56) References Cited

OTHER PUBLICATIONS

Zhang, X-Y., et al., "Additively Manufactured Scaffolds for Bone Tissue Engineering and the Prediction of their Mechanical Behavior: A Review," Materials, vol. 10 (50): 1-28 (2017).
U.S. Appl. No. 15/876,695, dated Jan. 22, 2018, Christopher L. Jones.
U.S. Appl. No. 16/251,383, dated Jan. 18, 2019, Christopher L. Jones.
U.S. Appl. No. 16/518,281, dated Jul. 22, 2019, Christopher L. Jones.
U.S. Appl. No. 15/876,793, dated Jan. 22, 2018, Christopher L. Jones.
U.S. Appl. No. 15/876,903, dated Jan. 22, 2018, Christopher L. Jones.
U.S. Appl. No. 15/877,002, dated Jan. 22, 2018, Christopher L. Jones.
U.S. Appl. No. 15/895,201, dated Feb. 13, 2018, Christopher L. Jones.
U.S. Appl. No. 16/565,321, dated Sep. 9, 2019, Christopher L. Jones.
U.S. Appl. No. 15/895,213, dated Feb. 13, 2018, Christopher L. Jones.
U.S. Appl. No. 15/895,228, dated Feb. 13, 2018, Christopher L. Jones.
U.S. Appl. No. 15/903,648, dated Feb. 23, 2018, Christopher L. Jones.
U.S. Appl. No. 15/903,667, dated Feb. 23, 2018, Christopher L. Jones.
U.S. Appl. No. 15/615,227, dated Jun. 6, 2017, Christopher L. Jones.
U.S. Appl. No. 15/942,846, dated Apr. 2, 2018, Christopher L. Jones.
European Search Report, 17810838.7, dated Dec. 19, 2019, 8 pages.
International Search Report and Written Opinion, PCT/US2019/043803, dated Nov. 7, 2019, 11 pages.

* cited by examiner

FLUID INTERFACE SYSTEM FOR IMPLANTS

CROSS REFERENCE TO RELATED APPLICATIONS

This application claims the benefit of U.S. Provisional Patent Application No. 62/480,388 filed Apr. 1, 2017, U.S. Provisional Patent Application No. 62/480,383 filed Apr. 1, 2017, U.S. Provisional Patent Application No. 62/480,393 filed Apr. 1, 2017, and U.S. Provisional Patent Application No. 62/619,260 filed Jan. 19, 2018, which are hereby incorporated by reference in their entirety.

FIELD OF THE INVENTION

The present invention relates to fluid interface systems for medical implants and, in particular, to fluid interface systems within implants comprised of a lattice or scaffold structure.

BACKGROUND OF THE INVENTION

During and after surgical procedures, it is often beneficial to add a fluid, whether it be blood or a drug, to an area of the surgical site. The use of various fluids, gels, putties, and other materials during surgery can minimize risks and increase the rate of recovery. For example, increasing blood and nutrients at the surgical site after an operation has been shown to increase the rate of recovery. Other examples of fluids that can be injected include bone marrow aspirate (BMA), stem cells, protein rich plasma (PRP), blood, fluid/bone mixtures, autograft tissue, allograft tissue, antibiotics, and other biologic agents or materials.

BRIEF SUMMARY OF THE INVENTION

The present invention provides a fluid interface system for medical implants. In some aspects, the fluid interface systems described herein can include one or more fluid interface channels disposed within an implant and optionally includes fluid redirection channels, fluid interface ports and a corresponding instrument to direct fluid into the fluid interface ports. In some embodiments, the fluid interface system is comprised of fluid interface channels contained within the interior of an implant. In some embodiments, the fluid interface channels may vary in diameter, permeability or density to optimize the delivery of a fluid. In some embodiments, fluid may enter the fluid interface channels through a fluid interface port located on the side of an implant.

Some embodiments of the fluid interface systems described herein can increase the uniformity of material or fluid packed into the open volume of devices comprising a lattice, open cell structure or porous volume. In some embodiments, it is important to achieve full distribution of material throughout such structures to maximally support tissue growth throughout such devices. The fluid interface systems described herein can provide one or more fluid interface channels to deliver fluids in difficult to access areas of a surgical site, increasing the uniformity of fluid distribution in devices.

The embodiments described herein are referred to as "fluid interface systems" because they can be used to distribute a fluid in or near a device and they can also be used to draw fluid in or near a device. The disclosed embodiments can be used in either mode, unless otherwise specified. It is appreciated that there are other possible modes known in the art that could be applicable to the present invention.

While the embodiments expressed herein are directed towards medical implants, the structures disclosed could also be beneficial when used in medical devices outside of the body that require the distribution or transport of fluid. Other medical devices that could include one or more systems described herein to accommodate the distribution or transport of a fluid include, but are not limited to, transcutaneous ports, fixation/posts or drains.

1R is a top sectioned view of a first exemplary embodiment of the invention adapted for use in an implant, showing an exemplary lateral spacing of the fluid interface channels.

Figure 2:
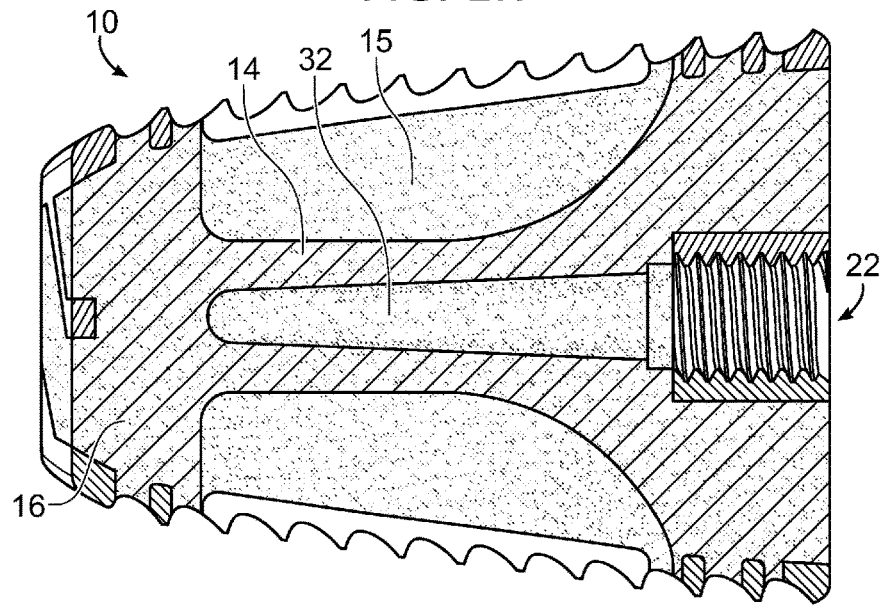

FIG. 2 is a side sectioned view of a first exemplary embodiment of the invention adapted for use in a first implant, sectioned vertically through horizontal center and showing the vertical distance of the center fluid interface channel from the upper and lower walls of the center arm.

Figure 3:
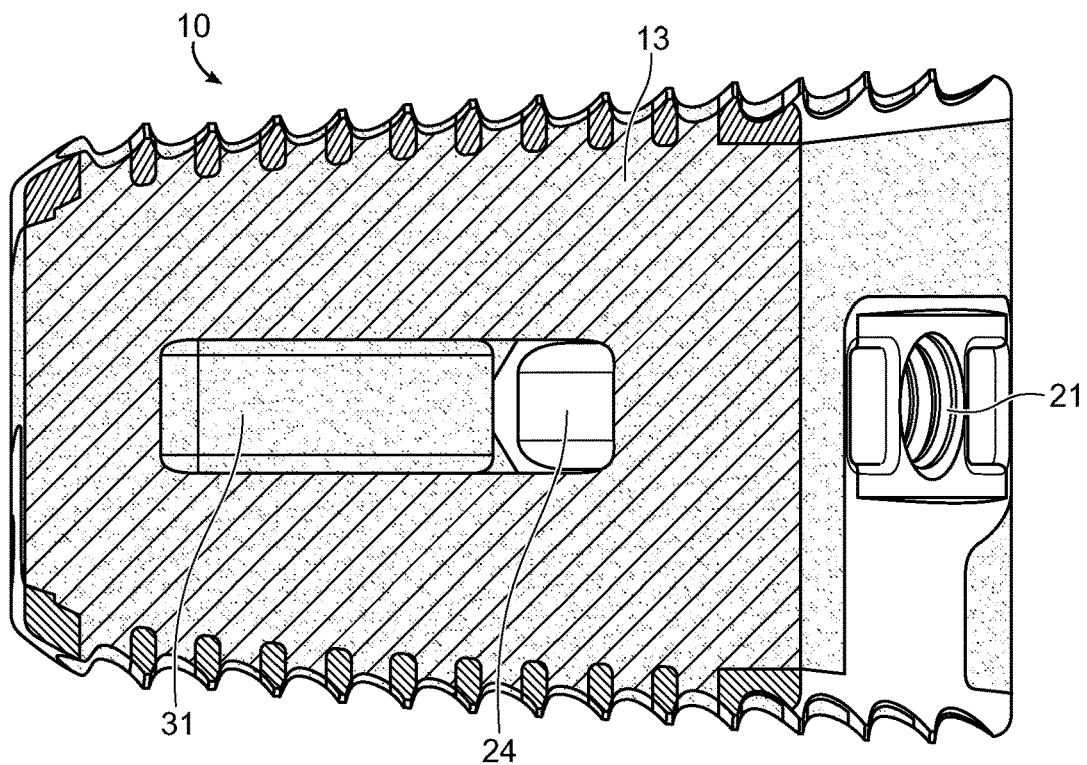

FIG. 3 is a side sectioned view of a first exemplary embodiment of the invention adapted for use in a first implant, sectioned vertically through line A in 1R and showing the configuration of the fluid interface channel in the left arm.

Figure 4:
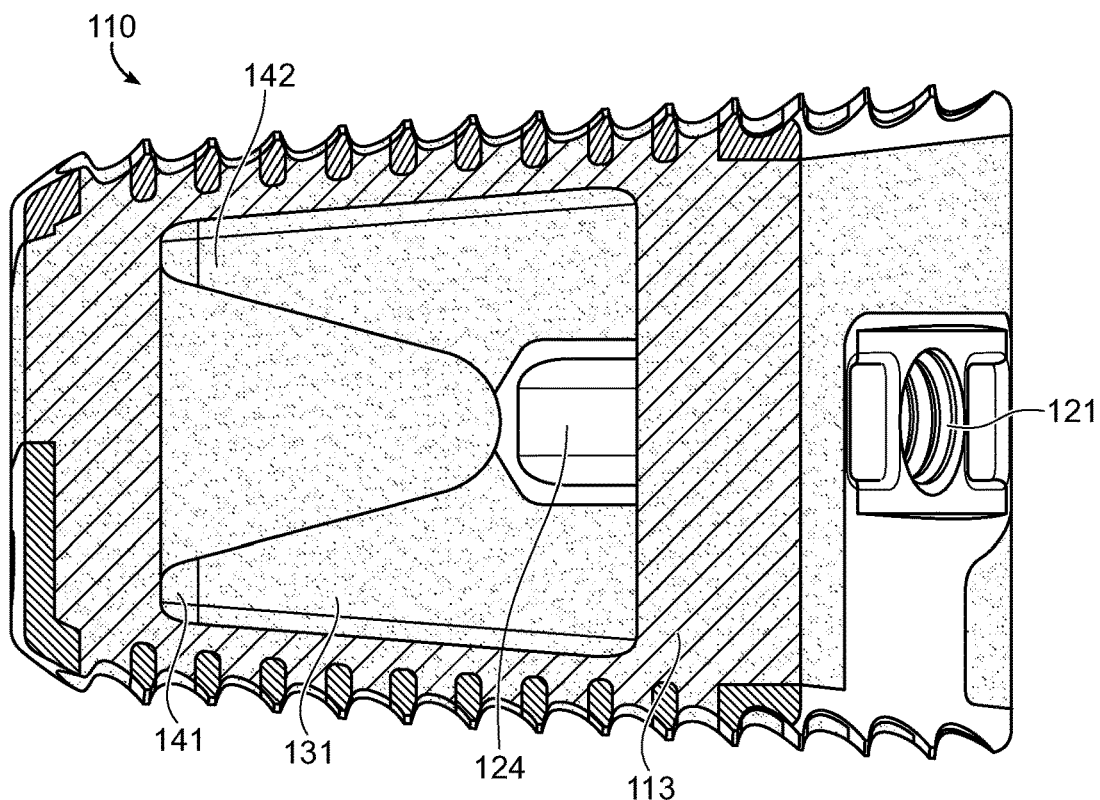

FIG. 4 is a side sectioned view of a second exemplary embodiment of the invention adapted for use in a second implant, sectioned vertically through a location similar to line A in 1R and showing an alternative configuration of the fluid interface channels with a spilt into multiple branches.

Figure 5:
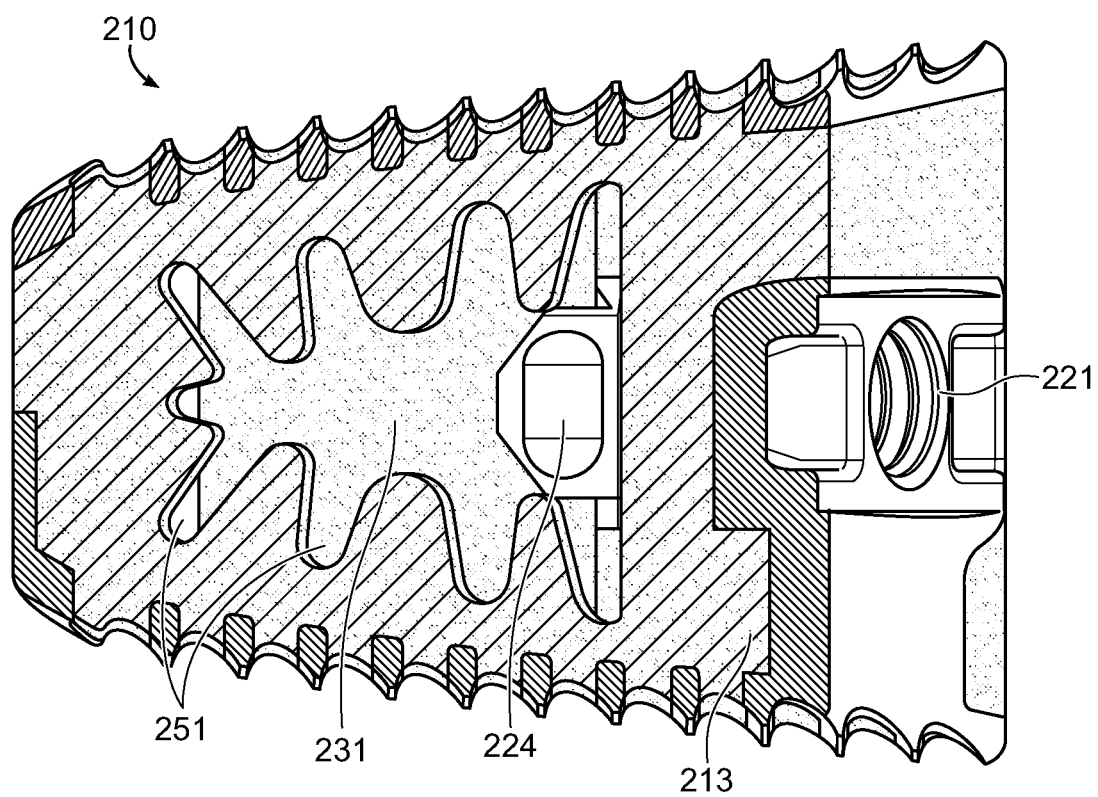

FIG. 5 is a side sectioned view of a third exemplary embodiment of the invention adapted for use in a third implant, sectioned vertically through a location similar to line A in 1R and showing an alternative configuration of the fluid interface channels with a plurality of branches.

Figure 6:
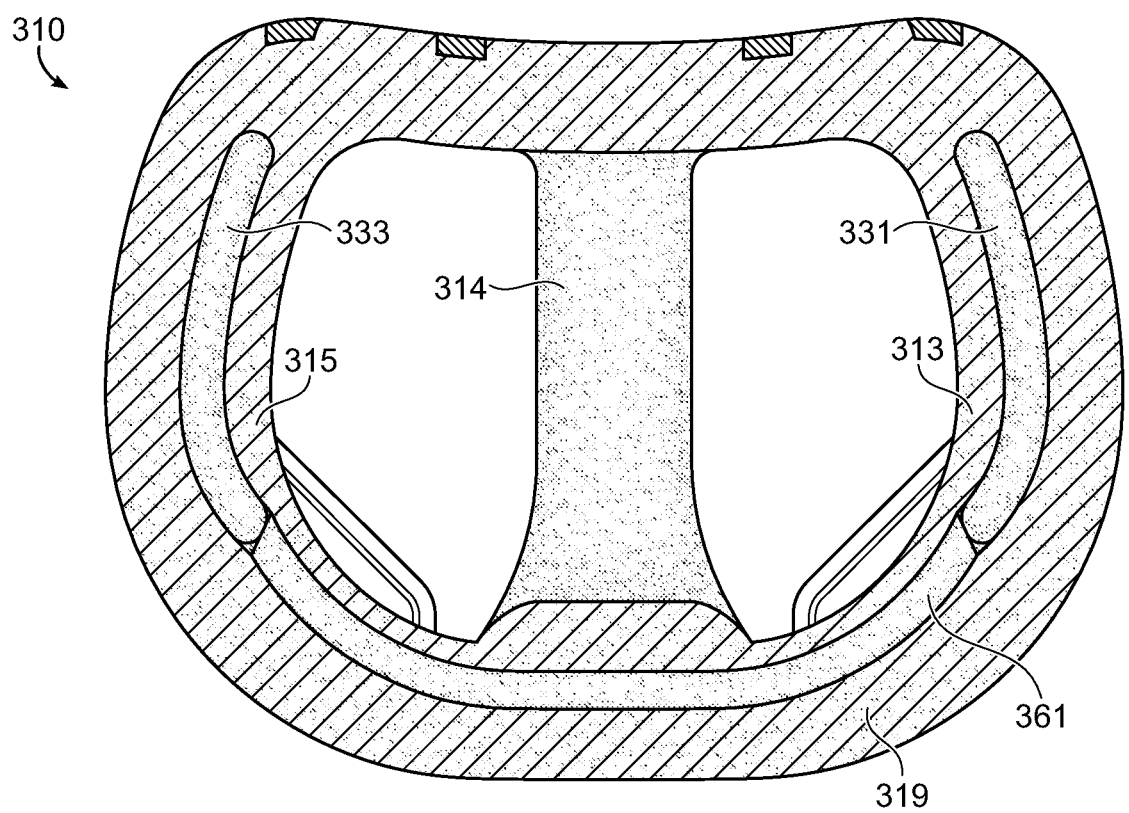

FIG. 6 is a bottom sectioned view of a fourth exemplary embodiment of the invention adapted for use in a fourth implant, showing the lateral spacing of the fluid interface channels and the inclusion of an optional linking channel to allow fluid to communicate laterally.

Figure 7:
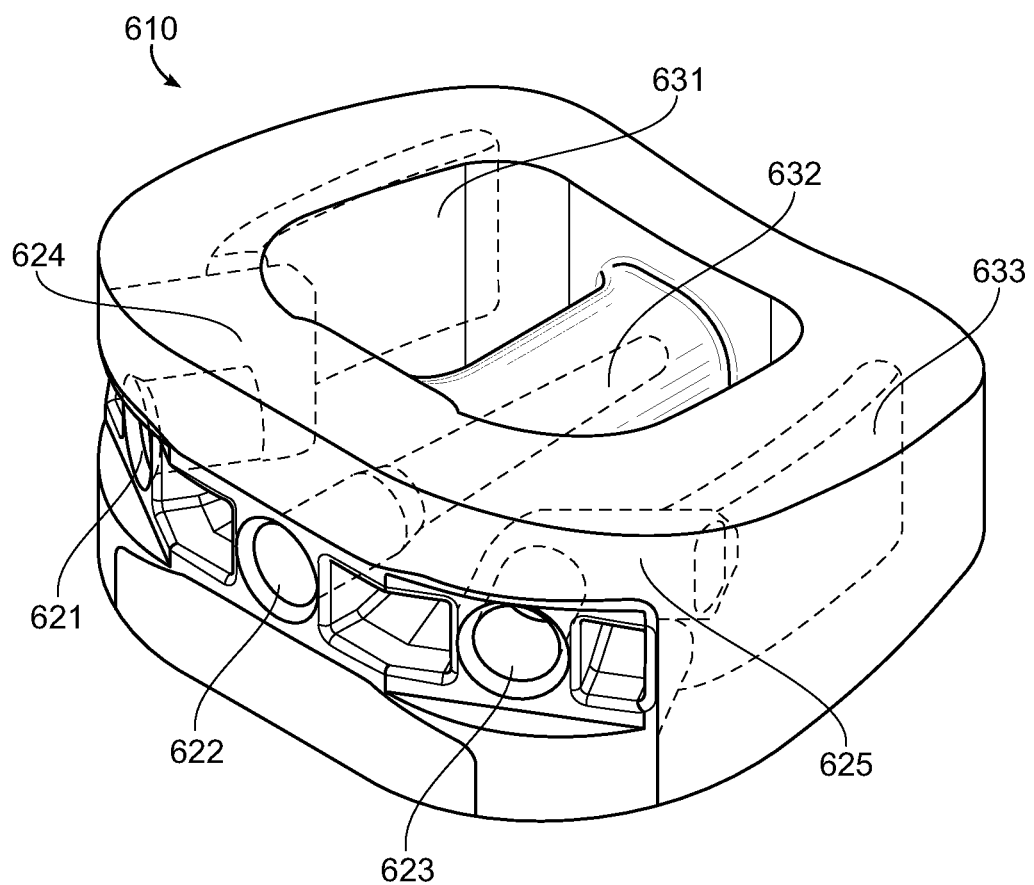

FIG. 7 is an isometric view of an exemplary fluid interface system included in an implant where the fluid interface system contained within the implant is represented by broken lines.

Figure 8:
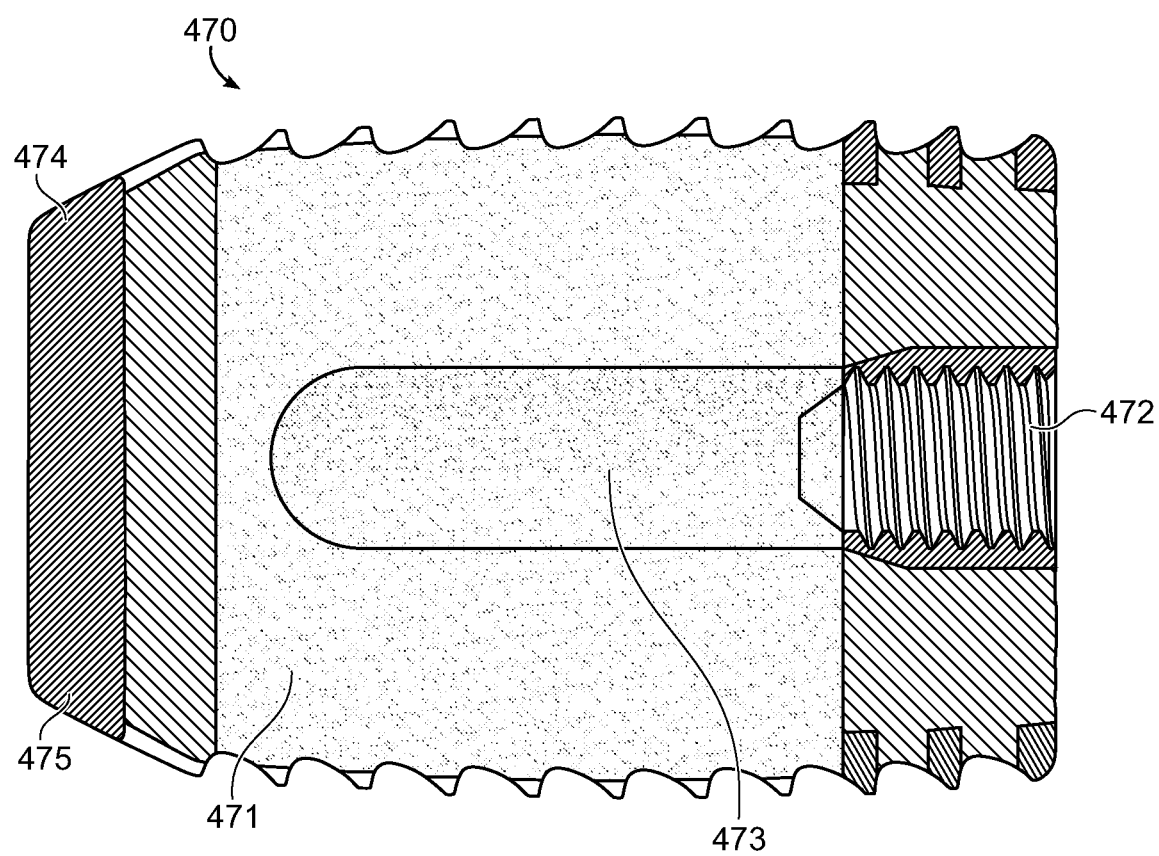

FIG. 8 is a side sectioned view of a fifth exemplary embodiment of the invention adapted for use in a fifth implant, showing an exemplary configuration for a fluid interface channel.

Figure 9:
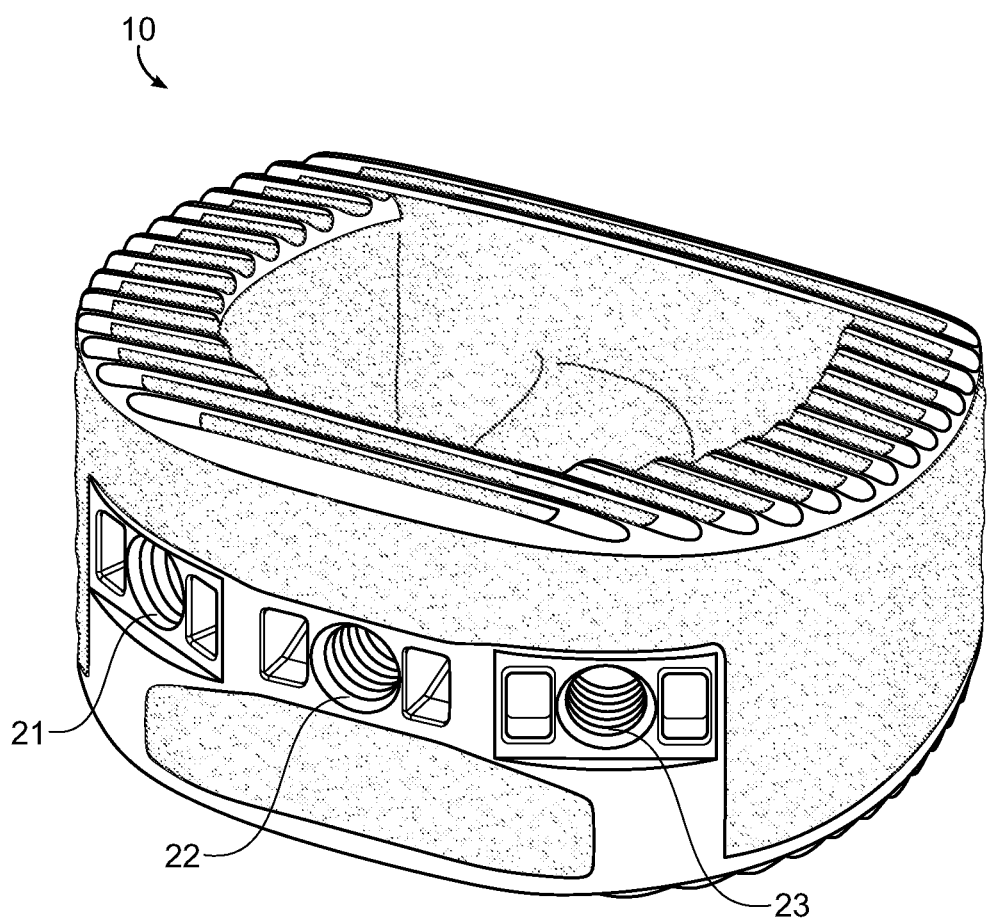

FIG. 9 is a perspective view of a first exemplary embodiment of the invention adapted for use in a first implant, showing the exemplary configuration of fluid interface ports on the anterior side of the implant.

Figure 10:
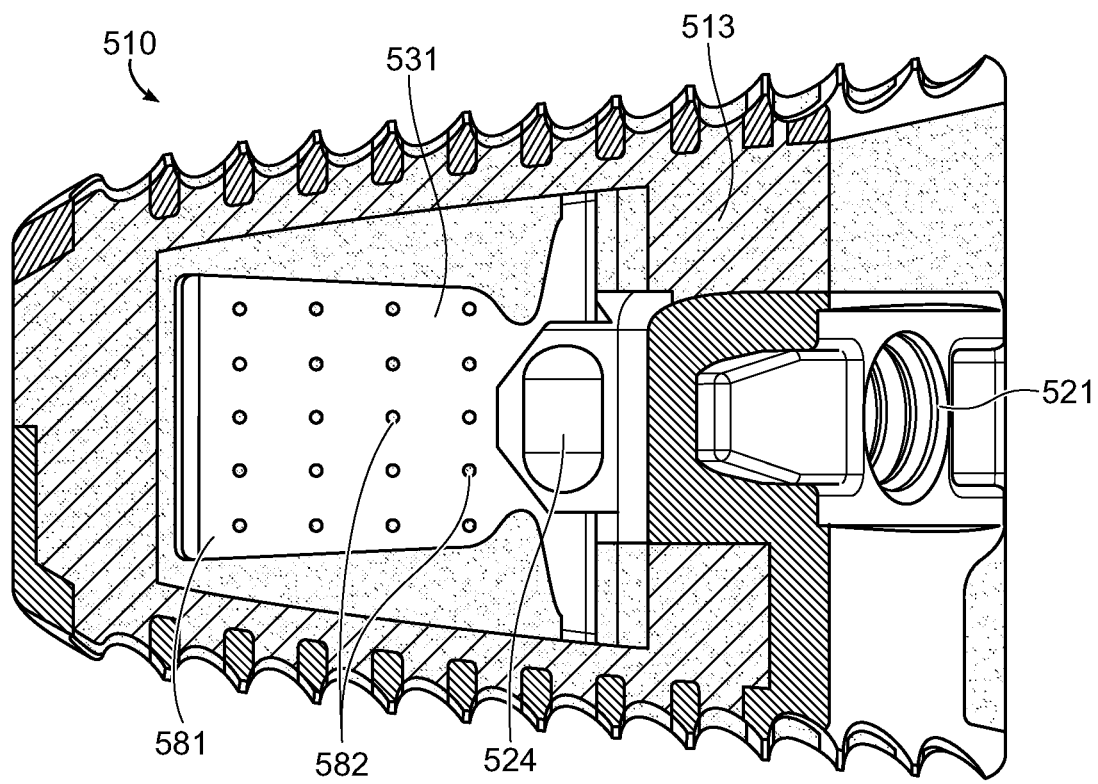

FIG. 10 is a side sectioned view of a sixth exemplary embodiment of the invention adapted for use in a sixth implant, sectioned vertically through a location similar to line A in 1R and showing an alternative configuration of the fluid interface channels with substantially solid walls and selectively placed pores.

DETAILED DESCRIPTION OF THE INVENTION

In many situations, it is desirable to use an implant that is capable of bone attachment or osteointegration over time. It is also desirable in many situations to use an implant that is capable of attachment or integration with living tissue. Examples of implants where attachment to bone or osteointegration is beneficial include, but are not limited to, cervical, lumbar, and thoracic interbody fusion implants, vertebral body replacements, osteotomy wedges, dental implants, bone stems, acetabular cups, cranio-facial plating, bone replacement and fracture plating. In many applications, it is also desirable to stress new bone growth to increase its strength. According to Wolff's law, bone will adapt to stresses placed on it so that bone under stress will grow stronger and bone that isn't stressed will become weaker.

In some aspects, the systems and methods described herein can be directed toward implants that are configured for osteointegration and stimulating adequately stressed new bone growth. Many of the exemplary implants of the present invention are particularly useful for use in situations where it is desirable to have strong bone attachment and/or bone growth throughout the body of an implant. Whether bone growth is desired only for attachment or throughout an implant, the present invention incorporates a unique lattice structure that can provide mechanical spacing, a scaffold to support new bone growth and a modulus of elasticity that allows new bone growth to be loaded with physiological forces. As a result, the present invention provides implants that grow stronger and healthier bone for more secure attachment and/or for a stronger bone after the implant osteointegrates.

The exemplary embodiments of the invention presented can be comprised, in whole or in part, of a lattice. A lattice, as used herein, refers to a three-dimensional material with one or more interconnected openings that allow a fluid to communicate from one location to another location through an opening. A three-dimensional material refers to a material that fills a three-dimensional space (i.e. has height, width and length). Lattices can be constructed by many means, including repeating various geometric shapes or repeating random shapes to accomplish a material with interconnected openings. An opening in a lattice is any area within the bounds of the three-dimensional material that is devoid of that material. Therefore, within the three-dimensional boundaries of a lattice, there is a volume of material and a volume that is devoid of that material.

The material that provides the structure of the lattice is referred to as the primary material. The structure of a lattice does not need to provide structural support for any purpose, but rather refers to the configuration of the openings and interconnections that comprise the lattice. An opening in a lattice may be empty, filled with a gaseous fluid, filled with a liquid fluid, filled with a solid or partially filled with a fluid and/or solid. Interconnections, with respect to openings, refer to areas devoid of the primary material and that link at least two locations together. Interconnections may be configured to allow a fluid to pass from one location to another location.

A lattice can be defined by its volumetric density, meaning the ratio between the volume of the primary material and the volume of voids presented as a percentage for a given three-dimensional material. The volume of voids is the difference between the volume of the bounds of the three-dimensional material and the volume of the primary material. The volume of voids can comprise of the volume of the openings, the volume of the interconnections and/or the volume of another material present. For example, a lattice with a 30% volumetric density would be comprised of 30% primary material by volume and 70% voids by volume over a certain volume. A lattice with a 90% volumetric density would be comprised of 90% primary material by volume and 10% voids by volume over a certain volume. In three-dimensional materials with a volumetric density of less than 50%, the volume of the primary material is less than the volume of voids. While the volumetric density refers to the volume of voids, the voids do not need to remain void and can be filled, in whole or in part, with a fluid or solid prior to, during or after implantation.

Lattices comprised of repeating geometric patterns can be described using the characteristics of a repeating unit cell. A unit cell in a repeating geometric lattice is a three-dimensional shape capable of being repeated to form a lattice. A repeating unit cell can refer to multiple identical unit cells that are repeated over a lattice structure or a pattern through all or a portion of a lattice structure. Each unit cell is comprised of a certain volume of primary material and a certain void volume, or in other words, a spot volumetric density. The spot volumetric density may cover as few as a partial unit cell or a plurality of unit cells. In many situations, the spot volumetric density will be consistent with the material's volumetric density, but there are situations where it could be desirable to locally increase or decrease the spot volumetric density.

Unit cells can be constructed in numerous volumetric shapes containing various types of structures. Unit cells can be bound by a defined volume of space to constrict the size of the lattice structure or other type of structure within the unit cell. In some embodiments, unit cells can be bound by volumetric shapes, including but not limited to, a cubic volume, a cuboid volume, a hexahedron volume or an amorphous volume. The unit cell volume of space can be defined based on a number of faces that meet at corners. In examples where the unit cell volume is a cubic, cuboid or hexahedron volume, the unit cell volume can have six faces and eight corners, where the corners are defined by the location where three faces meet. Unit cells may be interconnected in some or all areas, not interconnected in some or all areas, of a uniform size in some or all areas or of a nonuniform size in some or all areas. In some embodiments disclosed herein that use a repeating geometric pattern, the unit cells can be defined by a number of struts defining the edges of the unit cell and joined at nodes about the unit cell. Unit cells so defined can share certain struts among more than one unit cell, so that two adjacent unit cells may share a common planar wall defined by struts common to both cells. In some embodiments disclosed herein that use a repeating geometric pattern, the unit cells can be defined by a node and a number of struts extending radially from that node.

While the present application uses volumetric density to describe exemplary embodiments, it is also possible to describe them using other metrics, including but not limited to cell size, strut size or stiffness. Cell size may be defined using multiple methods, including but not limited to cell diameter, cell width, cell height and cell volume. Strut size may be defined using multiple methods, including but not limited to strut length and strut diameter.

Repeating geometric patterns are beneficial for use in lattice structures contained in implants because they can provide predictable characteristics. Many repeating geometric shapes may be used as the unit cell of a lattice, including but are not limited to, rhombic dodecahedron, diamond, dodecahedron, square, pentagonal, hexagonal, octagonal, sctet struts, trunic octa, diagonal struts, other known geometric structures, and rounded, reinforced, weakened, or simplified versions of each geometry.

Lattices may also be included in implants as a structural component or a nonstructural component. Lattices used in structural applications may be referred to herein as structural lattices, load-bearing lattices or stressed lattices. In some instances, structural lattices, load-bearing lattices or stressed lattices may be simply referred to as a lattice. Repeating geometric shaped unit cells, particularly the rhombic dodecahedron, are well suited, in theory, for use in structural lattices because of their strength to weight ratio. To increase the actual strength and fatigue resistance of a rhombic dodecahedron lattice, the present invention, in some embodiments, includes a modified strut comprised of triangular segments, rather than using a strut with a rectangular or circular cross section. Some embodiments herein also modify the angles defining the rhombic faces of a rhombic dodecahedron to change the lattice's elastic modulus and fatigue resistance.

The use of triangular segments provides a lattice with highly predictable printed properties that approach the theoretical strength values for a rhombic dodecahedron lattice.

In structural lattice applications, the strength and elastic modulus of the lattice can be approximated by the volumetric density. When the volumetric density increases, the strength and the elastic modulus increases. Compared to other porous structures, the lattice of the present invention has a higher strength and elastic modulus for a given volumetric density because of its ability to use the high strength to weight benefits of a rhombic dodecahedron, modified rhombic dodecahedron or radial dodeca-rhombus unit cell.

When configured to provide support for bone or tissue growth, a lattice may be referred to as a scaffold. Lattices can be configured to support bone or tissue growth by controlling the size of the openings and interconnections disposed within the three-dimensional material. A scaffold, if used on the surface of an implant, may provide an osteointegration surface that allows adjacent bone to attach to the implant. A scaffold may also be configured to provide a path that allows bone to grow further than a mere surface attachment. Scaffolds intended for surface attachment are referred to herein as surface scaffolds. A surface scaffold may be one or more unit cells deep, but does not extend throughout the volume of an implant. Scaffolds intended to support in-growth beyond mere surface attachment are referred to herein as bulk scaffolds. Scaffolds may also be included in implants as a structural component or a non-structural component. Scaffolds used in structural applications may be referred to herein as structural scaffolds, load-bearing scaffolds or stressed scaffolds. In some instances, structural scaffolds, load-bearing scaffolds or stressed scaffolds may be simply referred to as a scaffold. In some instances, the use of the term scaffold may refer to a material configured to provide support for bone or tissue growth, where the material is not a lattice.

The scaffolds described herein can be used to promote the attachment or in-growth of various types of tissue found in living beings. As noted earlier, some embodiments of the scaffold are configured to promote bone attachment and in-growth. The scaffolds can also be configured to promote attachment of in-growth of other areas of tissue, such as fibrous tissue. In some embodiments, the scaffold can be configured to promote the attachment or in-growth of multiple types of tissue. Some embodiments of the scaffolds are configured to be implanted near or abutting living tissue. Near living tissue includes situations where other layers, materials or coatings are located between a scaffold and any living tissue.

In some embodiments, the present invention uses bulk scaffolds with openings and interconnections that are larger than those known in the art. Osteons can range in diameter from about 100 µm and it is theorized that a bundle of osteons would provide the strongest form of new bone growth. Bone is considered fully solid when it has a diameter of greater than 3 mm so it is theorized that a bundle of osteons with a diameter equaling approximately half of that value would provide significant strength when grown within a scaffold. It is also theorized that osteons may grow in irregular shapes so that the cross-sectional area of an osteon could predict its strength. A cylindrical osteon growth with a 3 mm diameter has a cross-sectional area of approximately 7 square mm and a cylindrical osteon with a 1.5 mm diameter has a cross-sectional area of 1.8 square mm. It is theorized that an osteon of an irregular shape with a cross-sectional area of at least 1.8 square millimeters could provide a significant strength advantage when grown in a scaffold.

Most skilled in the art would indicate that pores or openings with a diameter or width between 300 μm to 900 μm, with a pore side of 600 μm being ideal, provide the best scaffold for bone growth. Instead, some embodiments of the present invention include openings and interconnections with a diameter or width on the order of 1.0 to 15.0 times the known range, with the known range being 300 μm to 900 μm, resulting in openings from 0.07 mm$^2$ up to 145 mm$^2$ cross sectional area for bone growth. In some examples, pores or openings with a diameter or width between and including 100 μm to 300 μm could be beneficial. Some examples include openings and interconnections with a diameter on the order of 1.0 to 5.0 times the known range. It has been at least theorized that the use of much larger openings and interconnections than those known in the art will allow full osteons and solid bone tissue to form throughout the bulk scaffold, allowing the vascularization of new, loadable bone growth. In some examples, these pores may be 3 mm in diameter or approximately 7 mm$^2$ in cross sectional area. In other examples, the pores are approximately 1.5 mm in diameter or approximately 1.75 mm$^2$ in cross sectional area. The use of only the smaller diameter openings and interconnections known in the art are theorized to limit the penetration of new bone growth into a bulk scaffold because the smaller diameter openings restrict the ability of vascularization throughout the bulk scaffold.

A related structure to a lattice is a closed cell material. A closed cell material is similar to a lattice, in that it has openings contained within the bounds of a three-dimensional material, however, closed cell materials generally lack interconnections between locations through openings or other pores. A closed cell structure may be accomplished using multiple methods, including the filling of certain cells or through the use of solid walls between the struts of unit cells. A closed cell structure can also be referred to as a cellular structure. It is possible to have a material that is a lattice in one portion and a closed cell material in another. It is also possible to have a closed cell material that is a lattice with respect to only certain interconnections between openings or vice versa. While the focus of the present disclosure is on lattices, the structures and methods disclosed herein can be easily adapted for use on closed cell structures within the inventive concept.

The lattice used in the present invention can be produced from a range of materials and processes. When used as a scaffold for bone growth, it is desirable for the lattice to be made of a biocompatible material that allows for bone attachment, either to the material directly or through the application of a bioactive surface treatment. In one example, the scaffold is comprised of an implantable metal. Implantable metals include, but are not limited to, zirconium, stainless steel (316 & 316L), tantalum, nitinol, cobalt chromium alloys, titanium and tungsten, and alloys thereof. Scaffolds comprised of an implantable metal may be produced using an additive metal fabrication or 3D printing process. Appropriate production processes include, but are not limited to, direct metal laser sintering, selective laser sintering, selective laser melting, electron beam melting, laminated object manufacturing and directed energy deposition.

In another example, the lattice of the present invention is comprised of an implantable metal with a bioactive coating. Bioactive coatings include, but are not limited to, coatings to accelerate bone growth, anti-thrombogenic coatings, anti-microbial coatings, hydrophobic or hydrophilic coatings, and hemophobic, superhemophobic, or hemophilic coatings. Coatings that accelerate bone growth include, but are not limited to, calcium phosphate, hydroxyapatite ("HA"), silicate glass, stem cell derivatives, bone morphogenic proteins, titanium plasma spray, titanium beads and titanium mesh. Anti-thrombogenic coatings include, but are not limited to, low molecular weight fluoro-oligomers. Anti-microbial coatings include, but are not limited to, silver, organosilane compounds, iodine and silicon-nitride. Superhemophobic coatings include fluorinated nanotubes.

In another example, the lattice is made from a titanium alloy with an optional bioactive coating. In particular, Ti6Al4V ELI wrought (American Society for Testing and Materials ("ASTM") F136) is a particularly well-suited titanium alloy for scaffolds. While Ti6Al4V ELI wrought is the industry standard titanium alloy used for medical purposes, other titanium alloys, including but not limited to, unalloyed titanium (ASTM F67), Ti6Al4V standard grade (ASTM F1472), Ti6Al7Nb wrought (ASTM 1295), Ti5Al2.5Fe wrought (British Standards Association/International Standard Organization Part 10), CP and Ti6Al4V standard grade powders (ASTM F1580), Ti13Nb13Zr wrought (ASTM F1713), the lower modulus Ti-24Nb-4Zr-8Sn and Ti12Mo6Zr2Fe wrought (ASTM F1813) can be appropriate for various embodiments of the present invention.

Titanium alloys are an appropriate material for scaffolds because they are biocompatible and allow for bone attachment. Various surface treatments can be done to titanium alloys to increase or decrease the level of bone attachment. Bone will attach to even polished titanium, but titanium with a surface texture allows for greater bone attachment. Methods of increasing bone attachment to titanium may be produced through a forging or milling process, sandblasting, acid etching, and the use of a bioactive coating. Titanium parts produced with an additive metal fabrication or 3D printing process, such as direct metal laser sintering, can be treated with an acid bath to reduce surface stress risers, normalize surface topography, and improve surface oxide layer, while maintaining surface roughness and porosity to promote bone attachment.

Additionally, Titanium or other alloys may be treated with heparin, heparin sulfate (HS), glycosaminoglycans (GAG), chondroitin-4-sulphate (C4S), chondroitin-6-sulphate (C6S), hyaluronan (HY), and other proteoglycans with or without an aqueous calcium solution. Such treatment may occur while the material is in its pre-manufacturing form (often powder) or subsequent to manufacture of the structure.

While a range of structures, materials, surface treatments and coatings have been described, it is believed that a lattice using a repeating modified rhombic dodecahedron (hereinafter "MRDD") unit cell can present a preferable combination of stiffness, strength, fatigue resistance, and conditions for bone ingrowth. In some embodiments, the repeating MRDD lattice is comprised of titanium or a titanium alloy. A generic rhombic dodecahedron (hereinafter "RDD"), by definition, has twelve sides in the shape of rhombuses. When repeated in a lattice, an RDD unit cell is comprised of 24 struts that meet at 14 vertices. The 24 struts define the 12 planar faces of the structure and disposed at the center of each planar face is an opening, or interconnection, allowing communication from inside the unit cell to outside the unit cell.

Figure 1A:
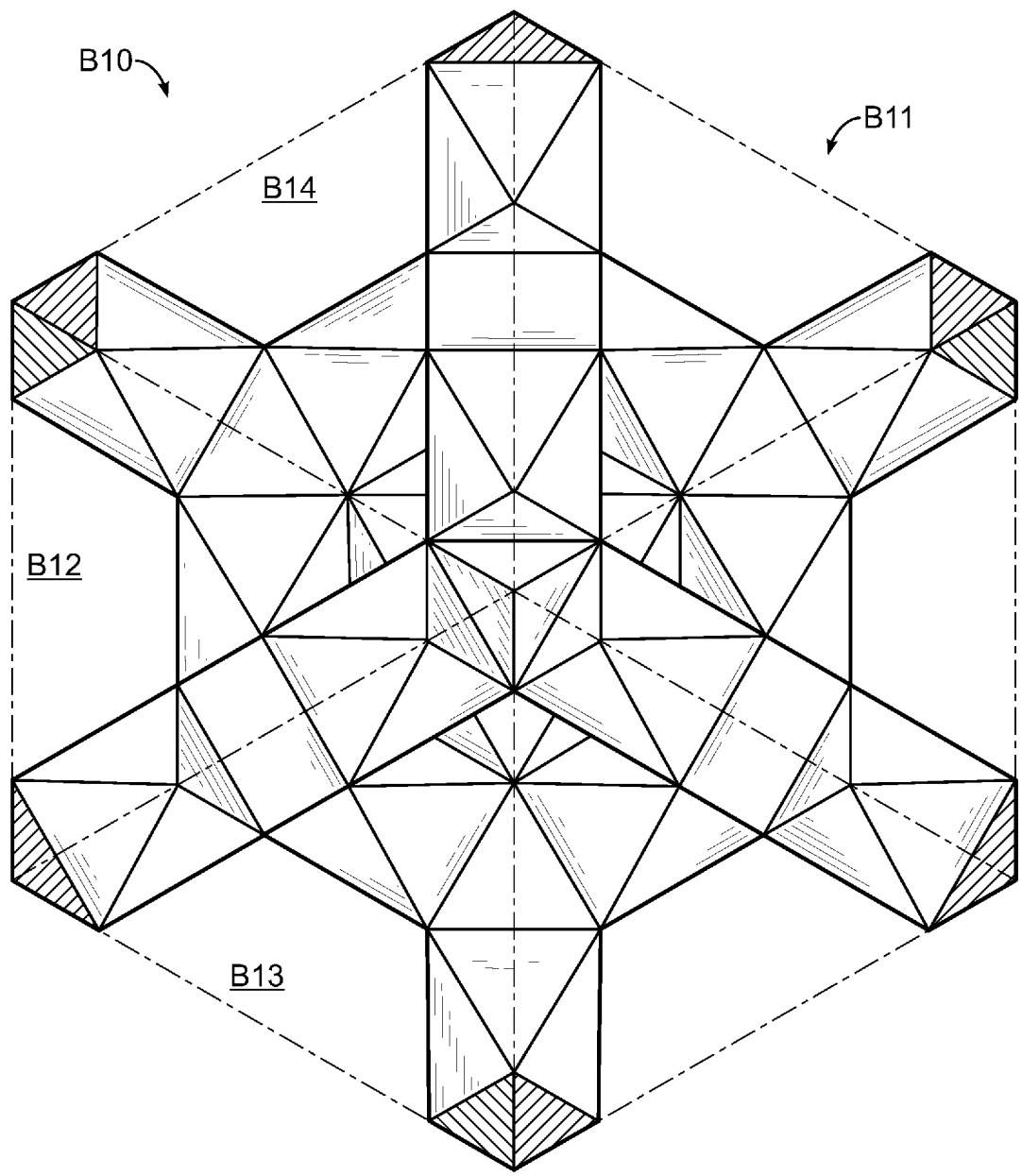
FIG. 1A is an isometric view of a single modified rhombic dodecahedron unit cell containing a full modified rhombic dodecahedron structure along with radial struts that comprise portions of adjacent unit cells.
Figure 1B:
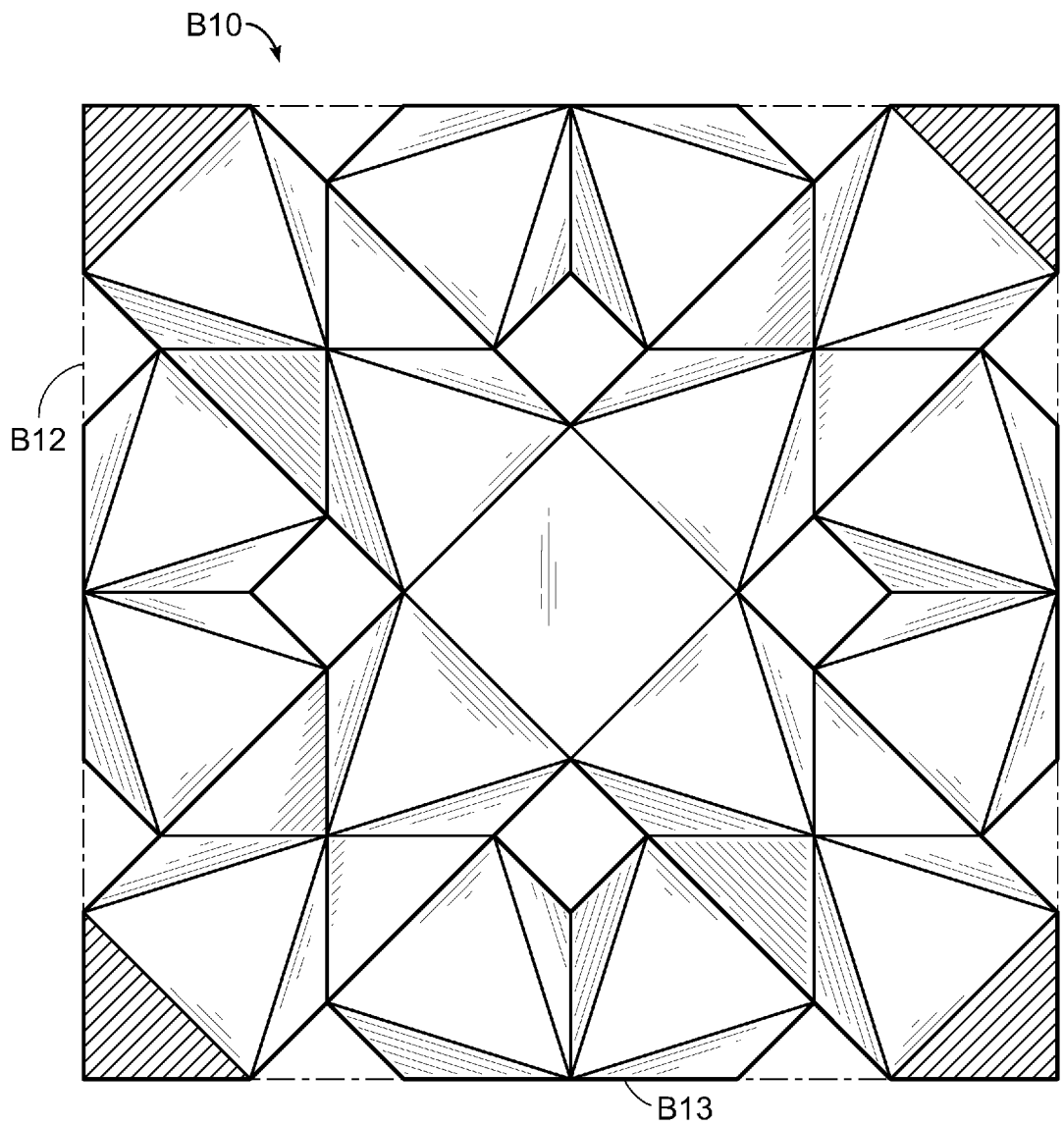
FIG. 1B is a side view of a single modified rhombic dodecahedron unit cell showing the configuration of interconnections when viewed from a lateral direction.

An example of the MRDD unit cell B10 used in the present invention is shown in FIGS. 1A-1E. In FIG. 1A is an isometric view of a single MRDD unit cell B10 containing a full MRDD structure along with radial struts that comprise portions of adjacent unit cells. In FIG. 1B is a side view of a single MRDD unit cell B10 showing the configuration of interconnections when viewed from a lateral direction. A top or bottom view of the MRDD unit cell B10 would be substantially the same as the side view depicted in FIG. 1B. The MRDD unit cell B10 differs in both structural characteristics and method of design from generic RDD shapes. A generic RDD is comprised of 12 faces where each face is an identical rhombus with an acute angle of 70.5 degrees and an obtuse angle of 109.5 degrees. The shape of the rhombus faces in a generic RDD do not change if the size of the unit cell or the diameter of the struts are changed because the struts are indexed based on their axis and each pass through the center of the 14 nodes or vertices.

In some embodiments of the MRDD, each node is contained within a fixed volume that defines its bounds and provides a fixed point in space for the distal ends of the struts. The fixed volume containing the MRDD or a sub-unit cell of the MRDD can be various shapes, including but not limited to, a cubic, cuboid, hexahedron or amorphous volume. Some examples use a fixed volume with six faces and eight corners defined by locations where three faces meet. The orientation of the struts can be based on the center of a node face at its proximate end and the nearest corner of the volume to that node face on its distal end. Each node is preferably an octahedron, more specifically a square bipyramid (i.e. a pyramid and inverted pyramid joined on a horizontal plane). Each node, when centrally located in a cuboid volume, more preferably comprises a square plane parallel to a face of the cuboid volume, six vertices and is oriented so that each of the six vertices are positioned at their closest possible location to each of the six faces of the cuboid volume. Centrally located, with regards to the node's location within a volume refers to positioning the node at a location substantially equidistant from opposing walls of the volume. In some embodiments, the node can have a volumetric density of 100 percent and in other embodiments, the node can have a volumetric density of less than 100 percent. Each face of the square bipyramid node can be triangular and each face can provide a connection point for a strut.

The struts can also be octahedrons, comprising an elongate portion of six substantially similar elongate faces and two end faces. The elongate faces can be isosceles triangles with a first internal angle, angle A, and a second internal angle, angle B, where angle B is greater than angle A. The end faces can be substantially similar isosceles triangles to one another with a first internal angle, angle C, and a second internal angle, angle D, where angle D is greater than angle C. Preferably, angle C is greater than angle A.

The strut direction of each strut is a line or vector defining the orientation of a strut and it can be orthogonal or non-orthogonal relative to the planar surface of each node face. In the MRDD and radial dodeca-rhombus structures disclosed herein, the strut direction can be determined using a line extending between the center of the strut end faces, the center of mass along the strut or an external edge or face of the elongate portion of the strut. When defining a strut direction using a line extending between the center of the strut end faces, the line is generally parallel to the bottom face or edge of the strut. When defining a strut direction using a line extending along the center of mass of the strut, the line can be nonparallel to the bottom face or edge of the strut. The octahedron nodes of the MRDD can be scaled to increase or decrease volumetric density by changing the origin point and size of the struts. The distal ends of the struts, however, are locked at the fixed volume corners formed about each node so that their angle relative to each node face changes as the volumetric density changes. Even as the volumetric density of an MRDD unit cell changes, the dimensions of the fixed volume formed about each node does not change. In FIG. 1A, dashed lines are drawn between the corners of the MRDD unit cell B10 to show the cube B11 that defines its bounds. In the MRDD unit cell in FIG. 1A, the height B12, width B13 and depth B14 of the unit cell are substantially the same, making the area defined by B11 a cube.

In some embodiments, the strut direction of a strut can intersect the center of the node and the corner of the cuboid volume nearest to the node face where the strut is fixed. In some embodiments, the strut direction of a strut can intersect just the corner of the cuboid volume nearest to the node face where the strut is fixed. In some embodiments, a reference plane defined by a cuboid or hexahedron face is used to describe the strut direction of a strut. When the strut direction of a strut is defined based on a reference plane, it can be between 0 degrees and 90 degrees from the reference plane. When the strut direction of a strut is defined based on a reference plane, it is preferably eight degrees to 30 degrees from the reference plane.

By indexing the strut orientation to a variable node face on one end and a fixed point on its distal end, the resulting MRDD unit cell can allow rhombus shaped faces with a smaller acute angle and larger obtuse angle than a generic RDD. The rhombus shaped faces of the MRDD can have two substantially similar opposing acute angles and two substantially similar opposing obtuse angles. In some embodiments, the acute angles are less than 70.5 degrees and the obtuse angles are greater than 109.5 degrees. In some embodiments, the acute angles are between 0 degrees and 55 degrees and the obtuse angles are between 125 degrees and 180 degrees. In some embodiments, the acute angles are between 8 degrees and 60 degrees and the obtuse angles are between 120 degrees and 172 degrees. The reduction in the acute angles increases fatigue resistance for loads oriented across the obtuse angle corner to far obtuse angle corner. The reduction in the acute angles and increase in obtuse angles also orients the struts to increase the MRDD's strength in shear and increases the fatigue resistance. By changing the rhombus corner angles from a generic RDD, shear loads pass substantially in the axial direction of some struts, increasing the shear strength. Changing the rhombus corner angles from a generic RDD also reduces overall deflection caused by compressive loads, increasing the fatigue strength by resisting deflection under load.

Figure 1C:
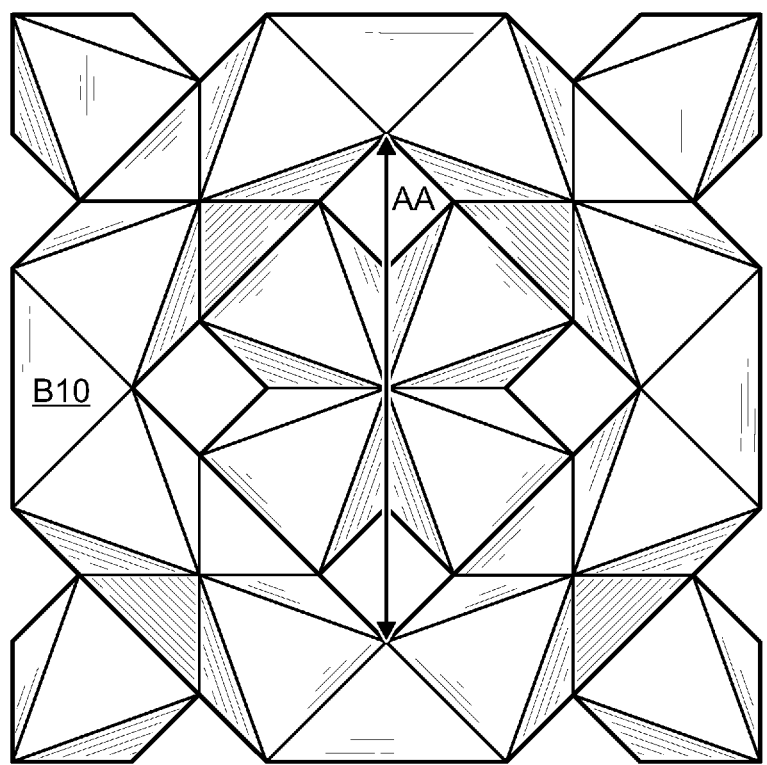
FIG. 1C is a side view of a single modified rhombic dodecahedron unit cell where the central void is being measured using the longest dimension method.
Figure 1D:
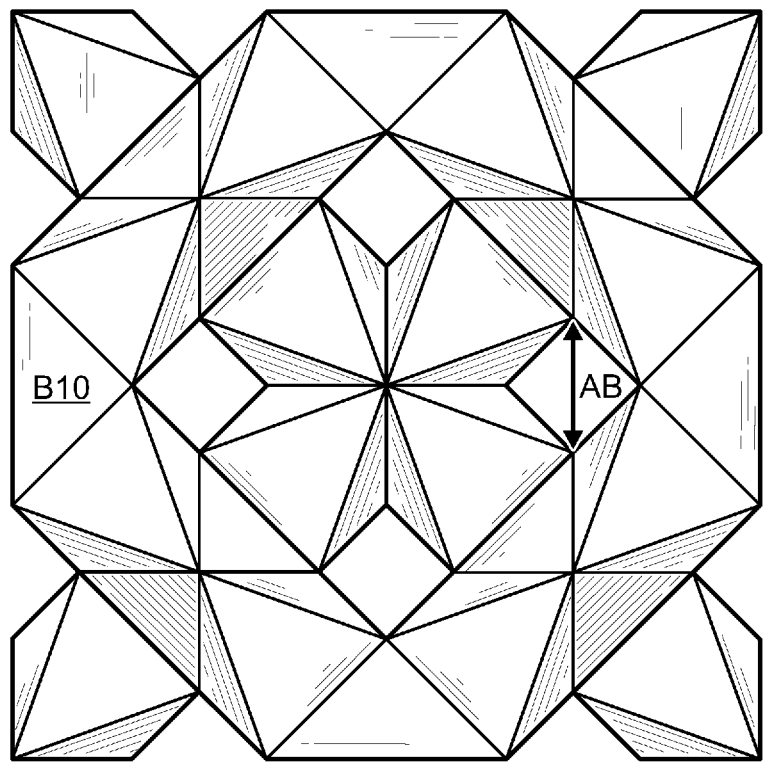
FIG. 1D is a side view of a single modified rhombic dodecahedron unit cell where an interconnection is being measured using the longest dimension method.

When placed towards the center of a lattice structure, the 12 interconnections of a unit cell connect to 12 different adjacent unit cells, providing continuous paths through the lattice. The size of the central void and interconnections in the MRDD may be defined using the longest dimension method as described herein. Using the longest dimension method, the central void can be defined by taking a measurement of the longest dimension as demonstrated in FIG. 1C. In FIG. 1C, the longest dimension is labeled as distance AA. The distance AA can be taken in the vertical or horizontal directions (where the directions reference the directions on the page) and would be substantially the same in this example. The interconnections may be defined by their longest measurement when viewed from a side, top or bottom of a unit cell. In FIG. 1D, the longest dimension is labeled as distance AB. The distance AB can be taken in the vertical or horizontal directions (where the directions reference the directions on the page). The view in FIG. 1D is a lateral view, however, in this example the unit cell will appear substantially the same when viewed from the top or bottom.

Figure 1E:
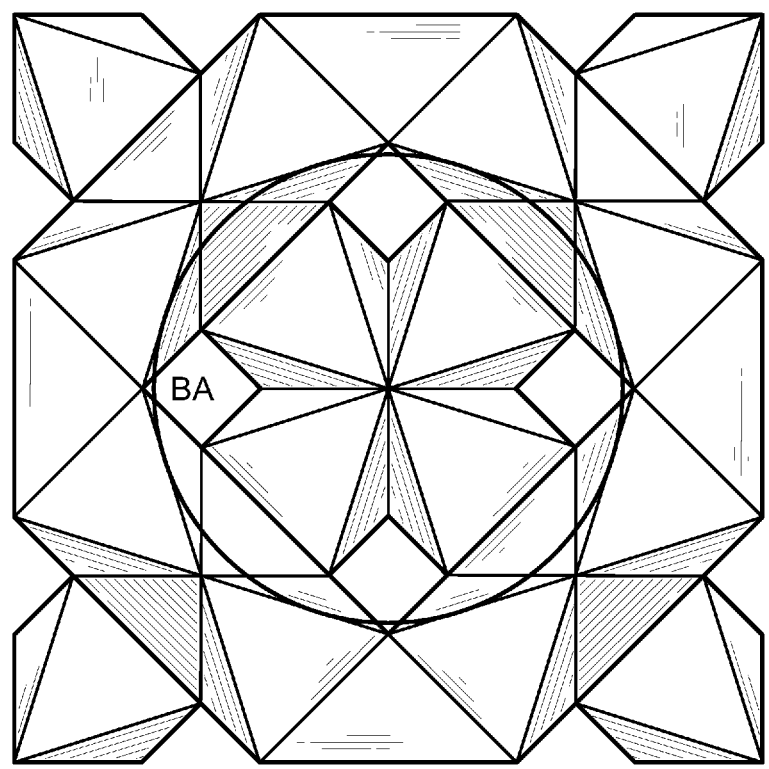
FIG. 1E is a side view of the central void of a modified rhombic dodecahedron unit cell being measured with the largest sphere method.
Figure 1F:
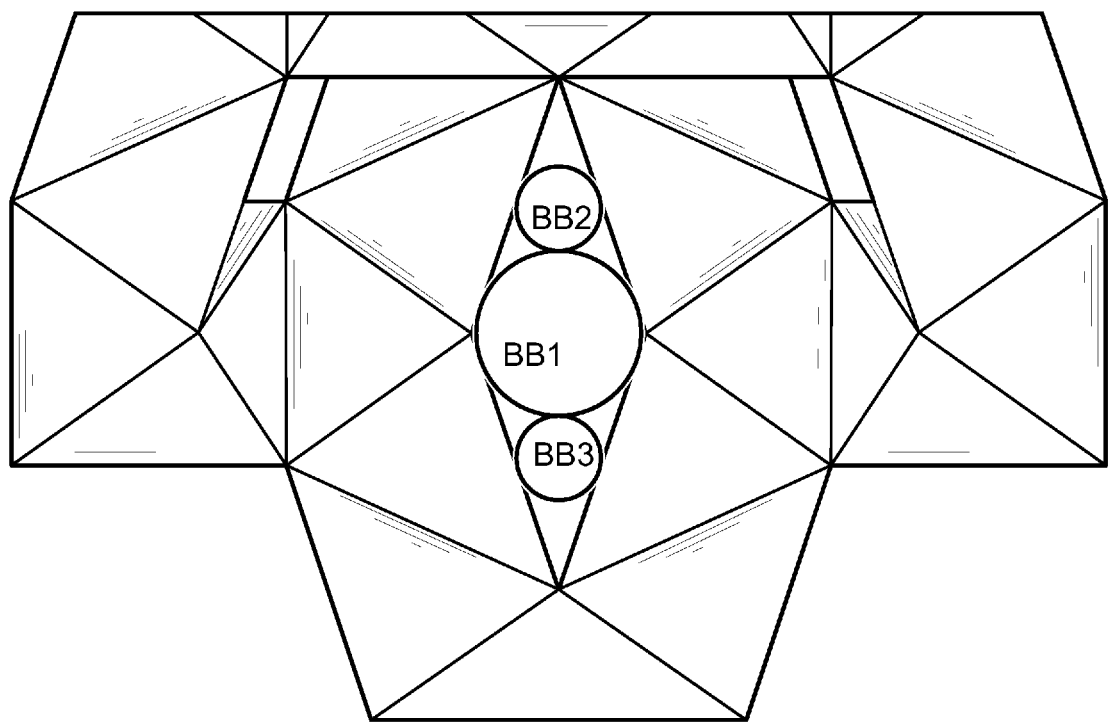
FIG. 1F is a view from a direction normal to the planar direction of an interconnection being measured with the largest sphere method.

The size of the central void and interconnections can alternatively be defined by the largest sphere method as described herein. Using the largest sphere method, the central void can be defined by the diameter of the largest sphere that can fit within the central void without intersecting the struts. In FIG. 1E is an example of the largest sphere method being used to define the size of a central void with a sphere with a diameter of BA. The interconnections are generally rhombus shaped and their size can alternatively be defined by the size of the length and width of three circles drawn within the opening. Drawn within the plane defining a side, a first circle BB1 is drawn at the center of the opening so that it is the largest diameter circle that can fit without intersecting the struts. A second circle BB2 and third circle BB3 is them drawn so that they are tangential to the first circle BB1 and the largest diameter circles that can fit without intersecting the struts. The diameter of the first circle BB1 is the width of the interconnection and the sum of the diameters of all three circles BB1, BB2 & BB3 represents the length of the interconnection. Using this method of measurement removes the acute corners of the rhombus shaped opening from the size determination. In some instances, it is beneficial to remove the acute corners of the rhombus shaped opening from the calculated size of the interconnections because of the limitations of additive manufacturing processes. For example, if an SLS machine has a resolution of 12 µm where the accuracy is within 5 µm, it is possible that the acute corner could be rounded by the SLS machine, making it unavailable for bone ingrowth. When designing lattices for manufacture on less precise additive process equipment, it can be helpful to use this measuring system to better approximate the size of the interconnections.

Using the alternative measuring method, in some examples, the width of the interconnections is approximately 600 µm and the length of the interconnections is approximately 300 µm. The use of a 600 µm length and 300 µm width provides an opening within the known pore sizes for bone growth and provides a surface area of roughly 1.8 square millimeters, allowing high strength bone growth to form. Alternative embodiments may contain interconnections with a cross sectional area of 1.0 to 15.0 times the cross-sectional area of a pore with a diameter of 300 µm. Other embodiments may contain interconnections with a cross sectional area of 1.0 to 15.0 times the cross-sectional area of a pore with a diameter of 900 µm.

The MRDD unit cell also has the advantage of providing at least two sets of substantially homogenous pore or opening sizes in a lattice structure. In some embodiments, a first set of pores have a width of about 200 µm to 900 µm and a second set of pores have a width of about 1 to 15 times the width of the first set of pores. In some embodiments, a first set of pores can be configured to promote the growth of osteoblasts and a second set of pores can be configured to promote the growth of osteons.

Pores sized to promote osteoblast growth can have a width of between and including about 100 µm to 900 µm. In some embodiments, pores sized to promote osteoblast growth can have a width that exceeds 900 µm. Pores sized to promote the growth of osteons can have a width of between and including about 100 µm to 13.5 mm. In some embodiments, pores sized to promote osteon growth can have a width that exceeds 13.5 mm.

In some embodiments, it is beneficial to include a number of substantially homogenous larger pores and a number of substantially homogenous smaller pores, where the number of larger pores is selected based on a ratio relative to the number of smaller pores. For example, some embodiments have one large pore for every one to 25 small pores in the lattice structure. Some embodiments preferably have one large pore for every eight to 12 smaller pores. In some embodiments, the number of larger and smaller pores can be selected based on a percentage of the total number of pores in a lattice structure. For example, some embodiments can include larger pores for four percent to 50 percent of the total number of pores and smaller pores for 50 percent to 96 percent of the total number of pores. More preferably, some embodiments can include larger pores for about eight percent to 13 percent of the total number of pores and smaller pores for about 87 percent to 92 percent of the total number of pores. It is believed that a lattice constructed with sets of substantially homogenous pores of the disclosed two sizes provides a lattice structure that simultaneously promotes osteoblast and osteon growth.

The MRDD unit cell may also be defined by the size of the interconnections when viewed from a side, top or bottom of a unit cell. The MRDD unit cell has the same appearance when viewed from a side, top or bottom, making the measurement in a side view representative of the others. When viewed from the side, as in FIG. 1D, an MRDD unit cell displays four distinct diamond shaped interconnections with substantially right angles. The area of each interconnection is smaller when viewed in the lateral direction than from a direction normal to the planar direction of each interconnection, but the area when viewed in the lateral direction can represent the area available for bone to grow in that direction. In some embodiments, it may be desirable to index the properties of the unit cell and lattice based on the area of the interconnections when viewed from the top, bottom or lateral directions.

In some embodiments of the lattice structures disclosed herein, the central void is larger than the length or width of the interconnections. Because the size of each interconnection can be substantially the same in a repeating MRDD structure, the resulting lattice can be comprised of openings of at least two discrete sizes. In some embodiments, it is preferable for the diameter of the central void to be approximately two times the length of the interconnections. In some embodiments, it is preferable for the diameter of the central void to be approximately four times the width of the interconnections.

In some embodiments, the ratio between the diameter of the central void and the length or width of the interconnections can be changed to create a structural lattice of a particular strength. In these embodiments, there is a correlation where the ratio between the central void diameter and the length or width of the interconnections increases as the strength of the structural lattice increases.

Figure 1G:
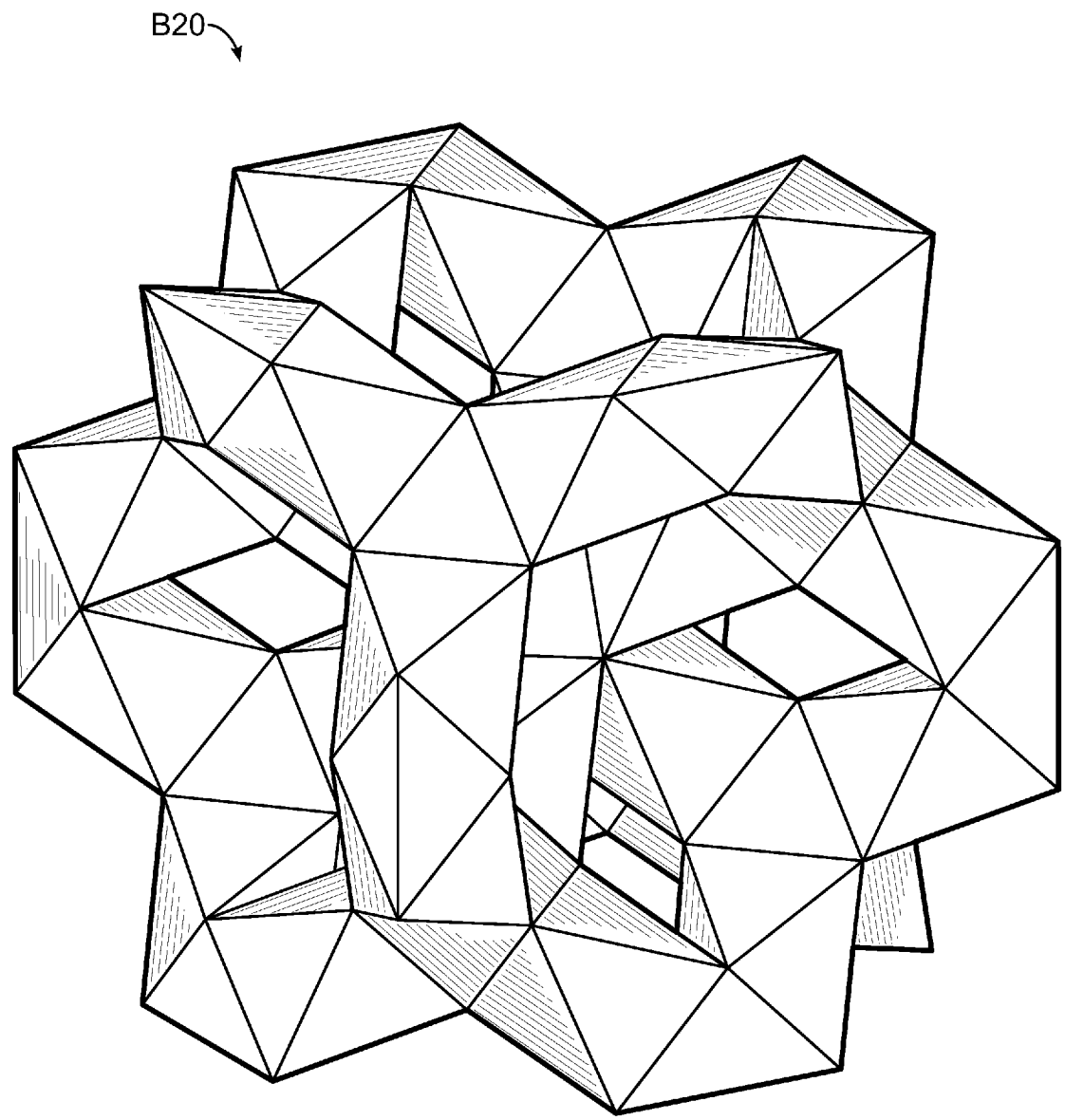
FIG. 1G is an isometric view of a single radial dodeca-rhombus unit cell.
Figure 1H:
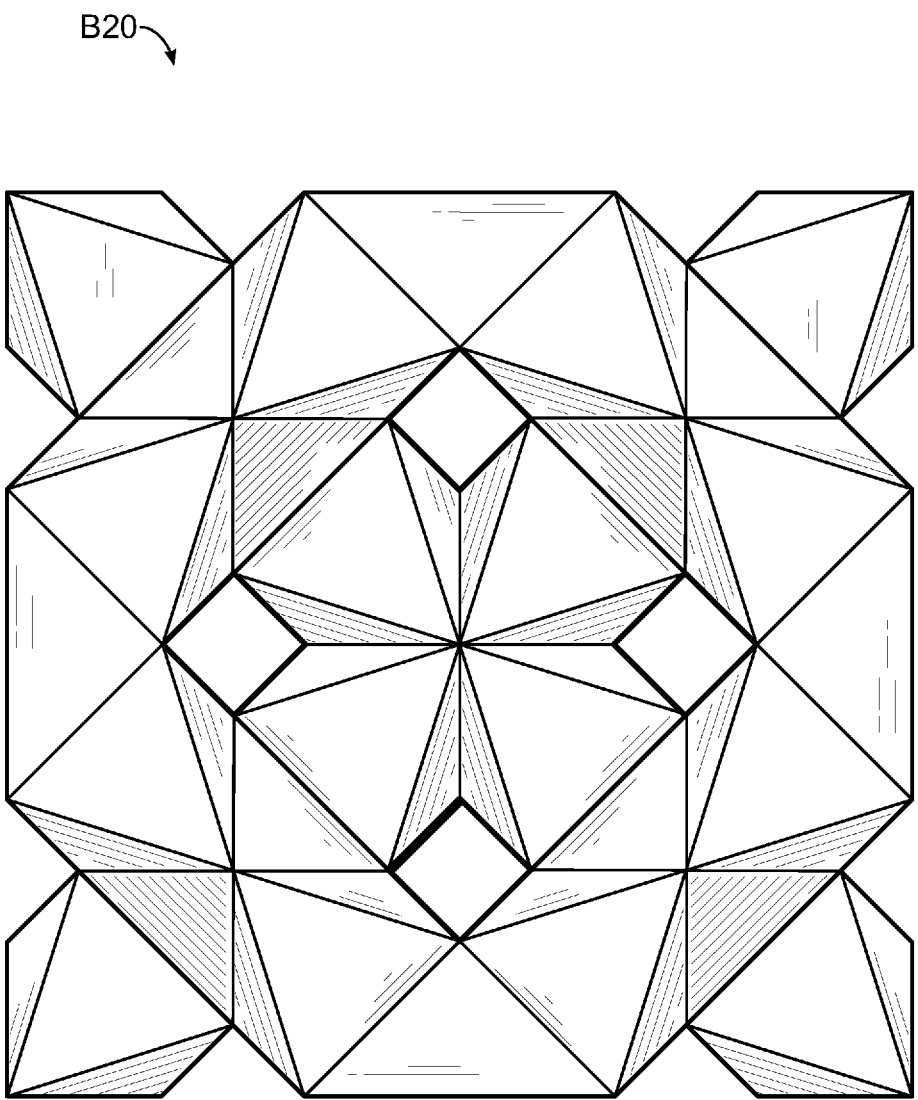
FIG. 1H is a side view of a single radial dodeca-rhombus unit cell.

It is also believed that a lattice using a repeating radial dodeca-rhombus (hereinafter "RDDR") unit cell can present a preferable combination of stiffness, strength, fatigue resistance, and conditions for bone ingrowth. In some embodiments, the repeating RDDR lattice is comprised of titanium or a titanium alloy. In FIG. 1G is an isometric view of a single RDDR unit cell B20 containing a full RDDR structure. In FIG. 1H is a side view of a single RDDR unit cell B20 showing the configuration of interconnections when viewed from a lateral direction. A top or bottom view of the RDDR unit cell B20 would be substantially the same as the side view depicted in FIG. 1H.

As used herein, an RDDR unit cell B20 is a three-dimensional shape comprised of a central node with radial struts and mirrored struts thereof forming twelve rhombus shaped structures. The node is preferably an octahedron, more specifically a square bipyramid (i.e. a pyramid and inverted pyramid joined on a horizontal plane). Each face of the node is preferably triangular and fixed to each face is a strut comprised of six triangular facets and two end faces. The central axis of each strut can be orthogonal or non-orthogonal relative to the planar surface of each node face. The central axis may follow the centroid of the strut. The RDDR is also characterized by a central node with one strut attached to each face, resulting in a square bipyramid node with eight struts attached.

Figure 1I:
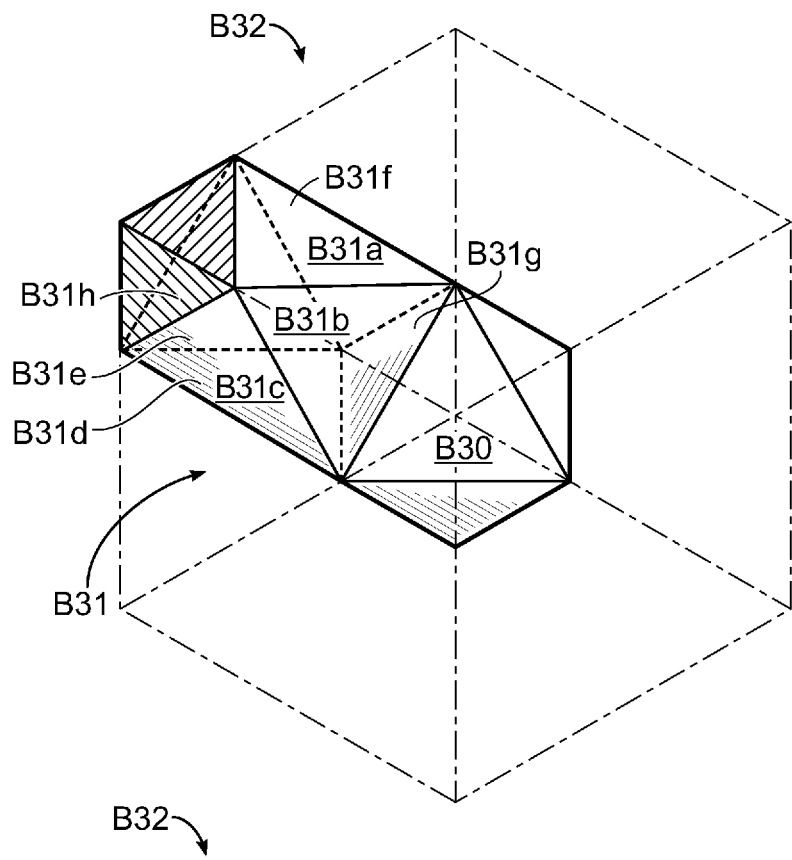
FIG. 1I is an isometric view of an example of a single node and single strut combination that could be used in a radial dodeca-rhombus unit cell.

Examples of node and strut combinations are shown in FIGS. 1I-1M. In FIG. 1I is an isometric view of a single node B30 with a single strut B31 attached. The node B30 is a square bipyramid oriented so that two peaks face the top and bottom of a volume B32 defining the bounds of the node B30 and any attached strut(s) B31. The node B30 is oriented so that the horizontal corners are positioned at their closest point to the lateral sides of the volume B32. The strut B31 extends from a node B30 face to the corner of the volume B32 defining the bounds of the node and attached struts. In FIG. 1I, the central axis of the strut is 45 degrees above the horizontal plane where the node's planar face is 45 degrees above a horizontal plane.

FIG. 1I also details an octahedron strut B31, where dashed lines show hidden edges of the strut. The strut B31 is an octahedron with an elongate portion of six substantially similar elongate faces and two end faces. The elongate faces B31a, B31b, B31c, B31d, B31e & B31f of the strut B31 define the outer surface of the strut's elongate and somewhat cylindrical surface. Each of the elongate faces B31a, B31b, B31c, B31d, B31e & B31f are isosceles triangles with a first internal angle, angle A, and a second internal angle, angle B, where angle B is greater than angle A. The strut B31 also has two end faces B31f & B31g that isosceles triangles that are substantially similar to one another, having a first internal angle, angle C, and a second internal angle, angle D, and where angle D is greater than angle C. When comparing the internal angles of the elongate faces B31a, B31b, B31c, B31d, B31e & B31f to the end faces B31f & B31g, angle C is greater than angle A.

Figure 1J:
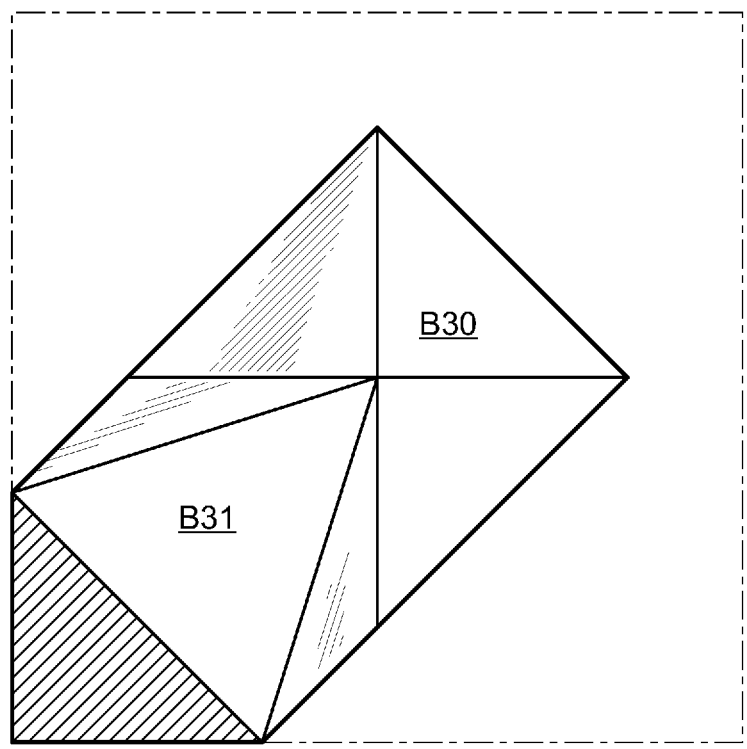
FIG. 1J is a side view of an example of a single node and single strut combination that could be used in a radial dodeca-rhombus unit cell.
Figure 1K:
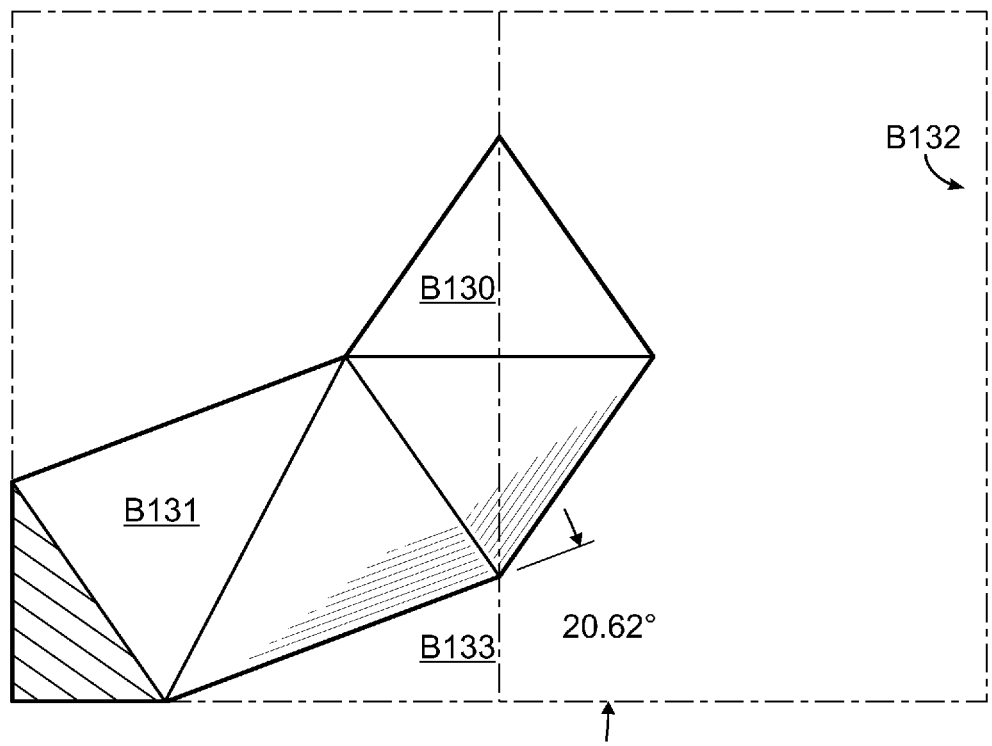
FIG. 1K is a side view of a single node and single strut combination configured for use in a lattice with an elastic modulus of approximately 3 GPa, viewed from the corner of the volume defining the bounds of the combination.
Figure 1L:
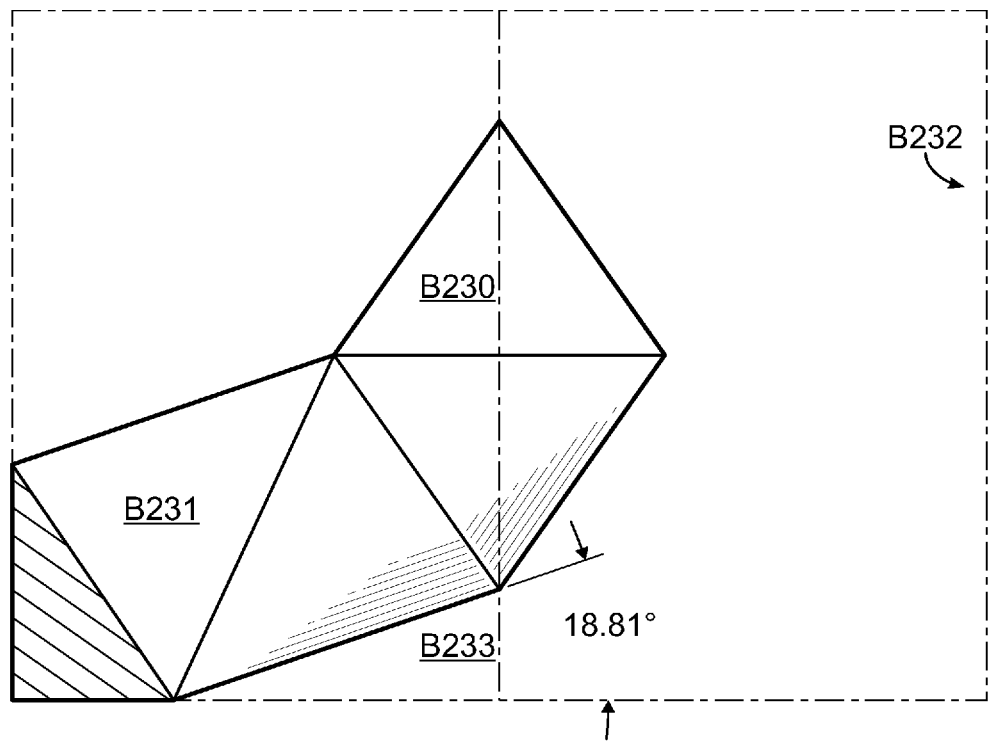
FIG. 1L is a side view of a single node and single strut combination configured for use in a lattice with an elastic modulus of approximately 4 GPa, viewed from the corner of the volume defining the bounds of the combination.
Figure 1M:
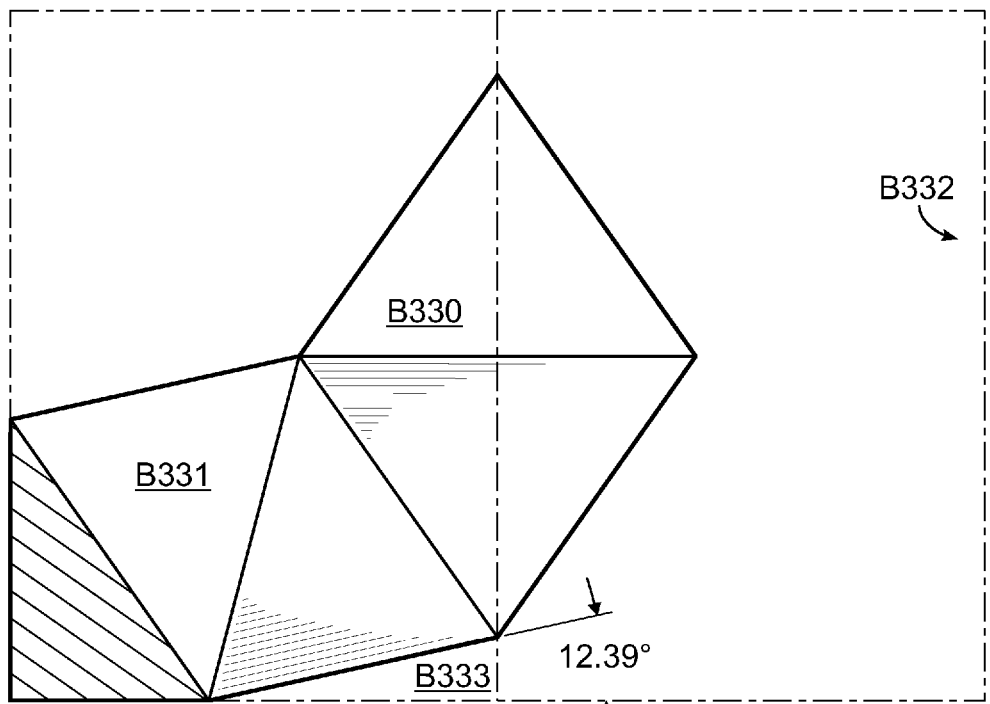
FIG. 1M is a side view of a single node and single strut combination configured for use in a lattice with an elastic modulus of approximately 10 GPa, viewed from the corner of the volume defining the bounds of the combination.

In FIG. 1J is a side view of the node B30 and strut B31 combination bounded by volume B32. In the side view, the height of the node B30 compared to the height of the cube B32 can be compared easily. In FIGS. 1K-1M are side views of node and strut combinations viewed from a corner of the volume rather than a wall or face, and where the combinations have been modified from FIGS. 1I-1J to change the volumetric density of the resulting unit cell. In FIG. 1K, the height of the node B130 has increased relative to the height of the volume B132. Since the distal end of the strut B131 is fixed by the location of a corner of the volume B132, the strut B131 must change its angle relative to its attached node face so that it becomes nonorthogonal. The node B130 and strut B131 combination, where the angle of the strut B131 from a horizontal plane is about 20.6 degrees, would be appropriate for a lattice structure with an elastic modulus of approximately 3 GPa.

In FIG. 1L, the height of the node B230 relative to the height of the cube B232 has been increased over the ratio of FIG. 1K to create a node B230 and strut B231 combination that would be appropriate for a lattice structure with an elastic modulus of approximately 4 GPa. As the height of the node B230 increases, the angle between the strut B231 and a horizontal plane decreases to about 18.8 degrees. As the height of the node B230 increases, the size of the node faces also increase so that the size of the strut B231 increases. While the distal end of the strut B231 is fixed to the corner of the volume B232, the size of the distal end increases to match the increased size of the node face to maintain a substantially even strut diameter along its length. As the node and strut increase in size, the volumetric density increases, as does the elastic modulus. In FIG. 1M, the height of the node B330 relative to the height of the volume B332 has been increased over the ratio of FIG. 1M to create a node B330 and strut B331 combination that would be appropriate for a lattice structure with an elastic modulus of approximately 10 GPa. In this configuration, the angle B333 between the strut B331 and a horizontal plane decreases to about 12.4 degrees and the volumetric density increases over the previous examples. The single node and strut examples can be copied and/or mirrored to create unit cells of appropriate sizes and characteristics. For instance, the angle between the strut and a horizontal plane could be increased to 25.8 degrees to render a lattice with a 12.3 percent volumetric density and an elastic modulus of about 300 MPa. While a single node and single strut were shown in the examples for clarity, multiple struts may be attached to each node to create an appropriate unit cell.

Adjacent struts extending from adjacent node faces on either the upper half or lower half of the node have an angle from the horizontal plane and a lateral separation angle defined by an angle between the strut directions of adjacent struts. In the MRDD and RDDR structures, adjacent struts have an external edge or face of the elongate portion extending closest to the relevant adjacent strut. The lateral separation angle, as used herein, generally refers to the angle between an external edge or face of the elongate portion of a strut extending closest to the relevant adjacent strut. In some embodiments, a lateral separation angle defined by a line extending between the center of the strut end faces or a line defined by the center of mass of the struts can be used in reference to a similar calculation for an adjacent strut.

Figure 1N:
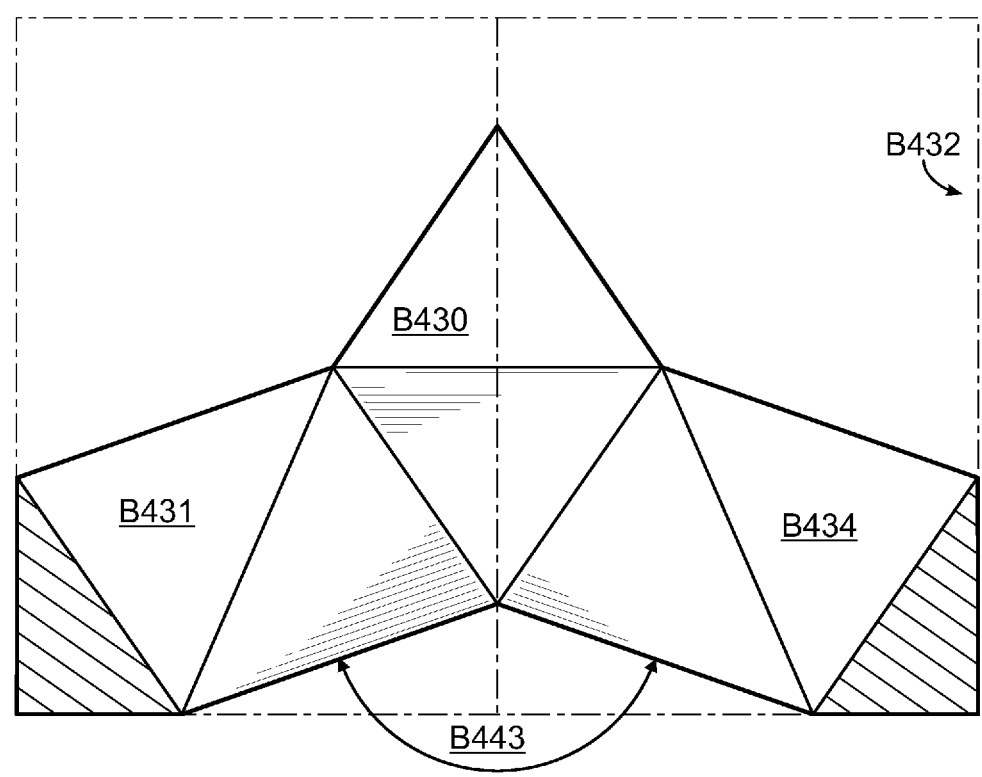
FIG. 1N is a side view of a single node and two adjacent struts viewed from the corner of the volume defining the bounds of the combination and the lateral separation angle.

The lateral separation angle is the angle between the nearest face or edge of a strut to an adjacent strut. The lateral separation angle can be measured as the smallest angle between the nearest edge of a strut to the nearest edge of an adjacent strut, in a plane containing both strut edges. The lateral separation angle can also be measured as the angle between the nearest face of a strut to the nearest face of an adjacent strut in a plane normal to the two strut faces. In embodiments without defined strut edges or strut faces, the lateral separation angle can be measured as an angle between the nearest portion of one strut to the nearest portion of an adjacent strut. For a unit cell in a cubic volume, as the strut angle from the horizontal plane decreases, the lateral separation angle approaches 90 degrees. For a unit cell in a cubic volume, as the strut angle from the horizontal plane increases, the lateral separation angle approaches 180 degrees. In some embodiments, it is preferable to have a lateral separation angle greater than 109.5 degrees. In some embodiments, it is preferable to have a lateral separation angle of less than 109.5 degrees. In some embodiments, it is preferable to have a lateral separation angle of between and including about 108 degrees to about 156 degrees. In some embodiments, it is more preferable to have a lateral separation angle of between and including 111 degrees to 156 degrees. In some embodiments, it is more preferable to have a lateral separation angle of between and including 108 degrees to 120 degrees. In some embodiments, it is most preferable to have a lateral separation angle of between and including about 111 degrees to 120 degrees. In some embodiments, it is more preferable to have a lateral separation angle of between and including 128 degrees to 156 degrees. In FIG. 1N is a side view, viewed from a corner of the cube B432, of a single node B430 with two adjacent struts B431 & B434 attached and where the lateral separation angle B443 is identified. When measured from the nearest edge of a strut to the nearest edge of an adjacent strut, the lateral separation angle B443 is about 116 degrees.

Figure 1P:
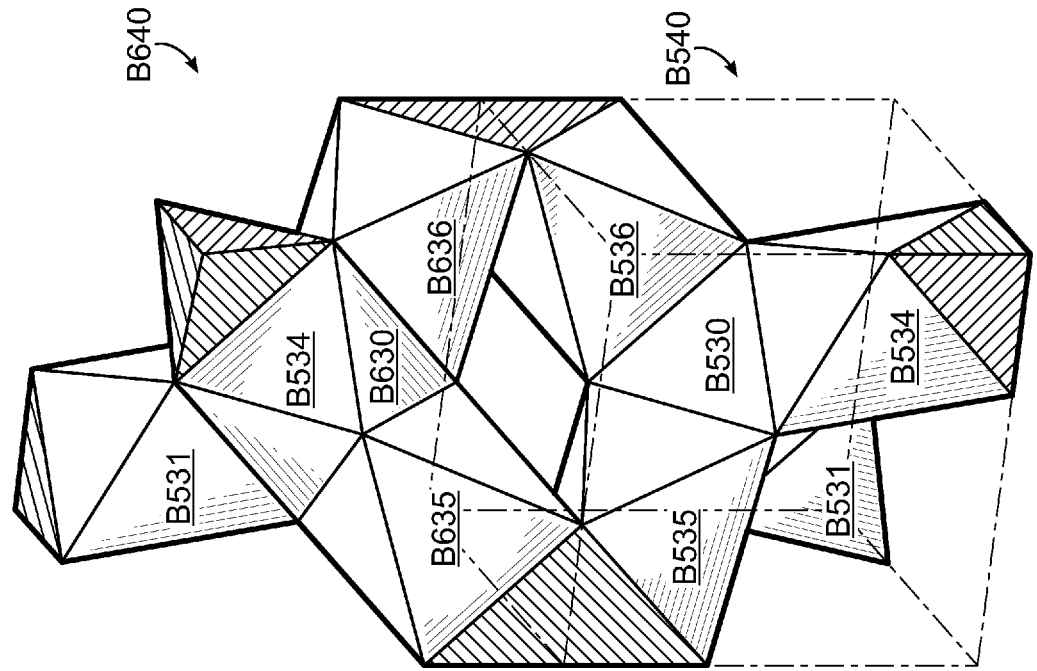
FIG. 1P is an isometric view of two sub-unit cells in a stacked formation where the upper sub-unit cell is inverted and fixed to the top of the lower sub-unit cell.
Figure 1O:
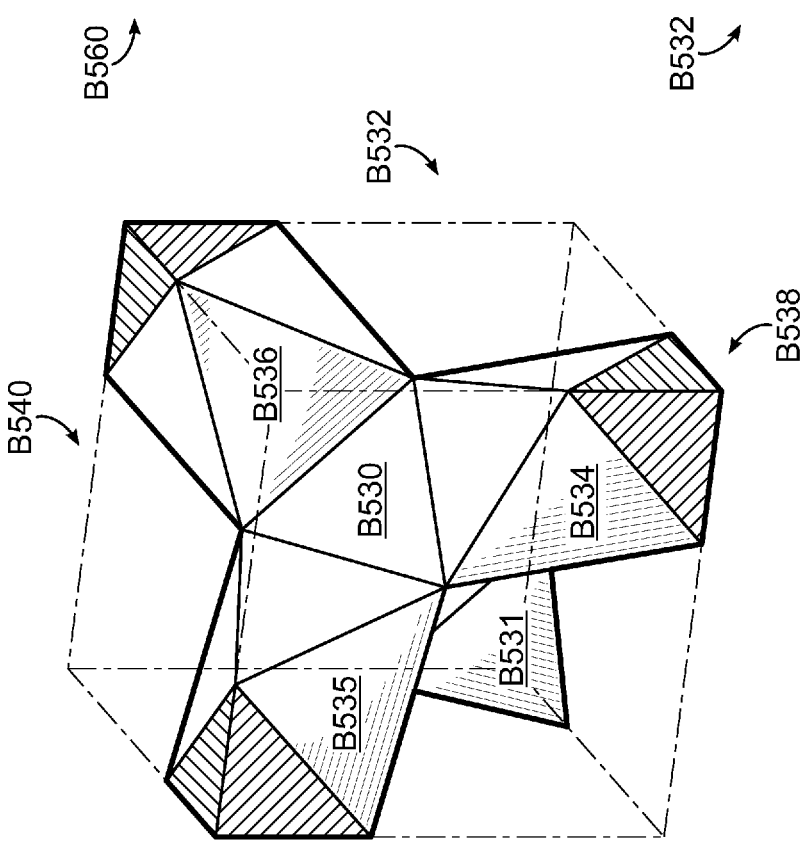
FIG. 1O is an isometric view of a sub-unit cell comprised of a single node and four struts.
Figure 1Q:
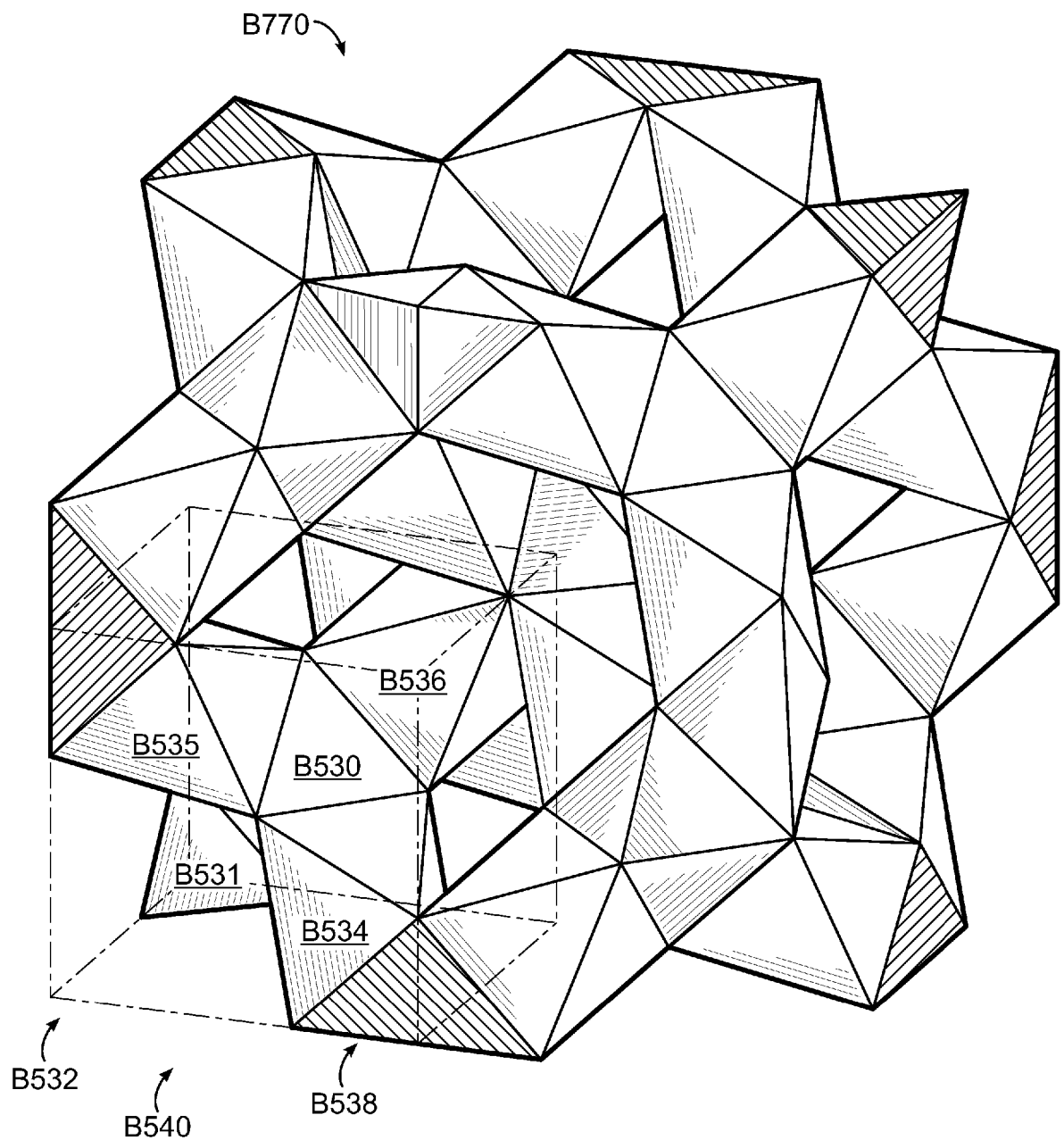
FIG. 1Q is an isometric view of eight sub-unit cells stacked together to form a single unit cell.
Figure 1R:
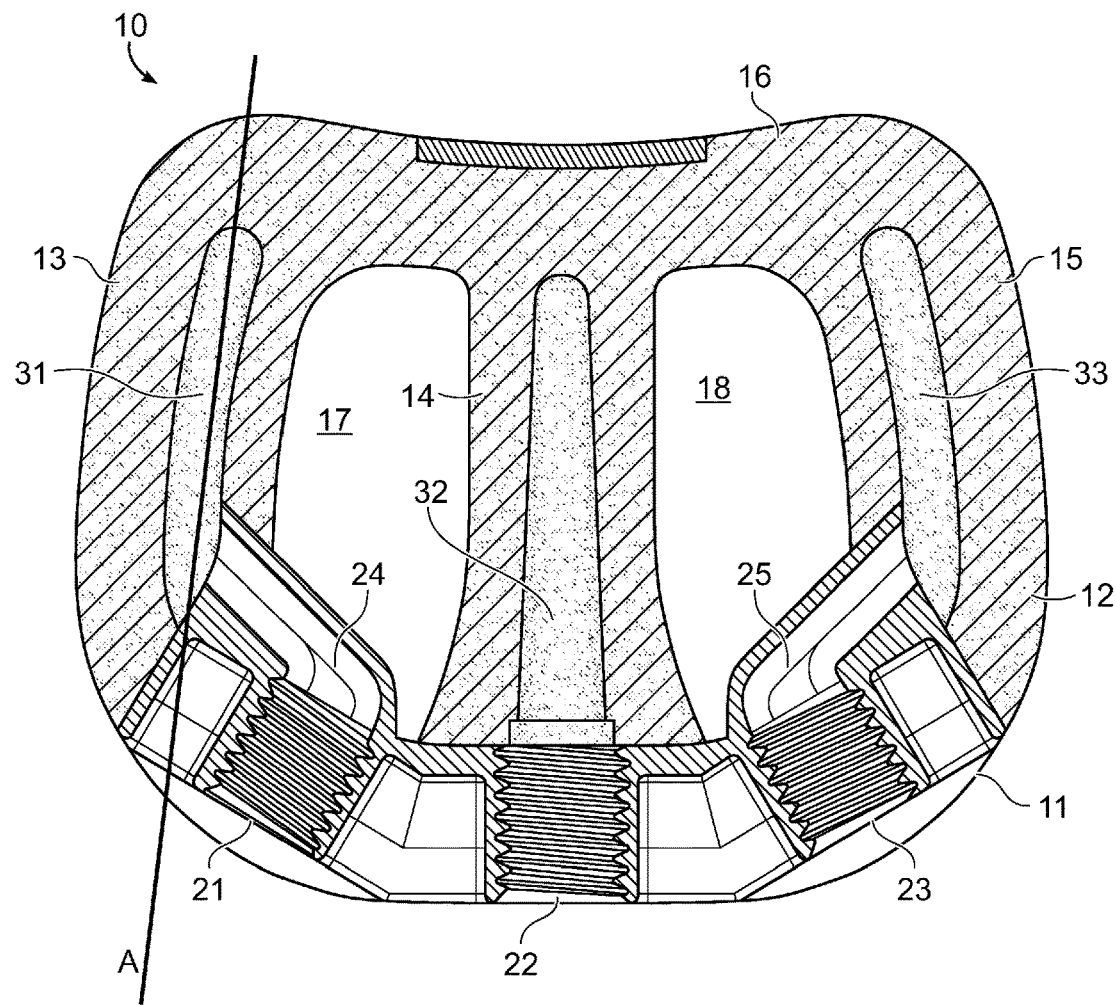

In some embodiments, a unit cell is built up from multiple sub-unit cells fixed together. In FIG. 1O is an isometric view of an exemplary sub-unit cell comprising a single node and four struts. In FIG. 1P is an isometric view of two sub-unit cells in a stacked formation where the upper sub-unit cell is inverted and fixed to the top of the lower sub-unit cell. In FIG. 1Q is an isometric view of eight sub-unit cells stacked together to form a single RDDR unit cell.

In FIG. 1O, the node B530 is a square bipyramid, oriented so that the two peaks face the top and bottom of a cubic volume B532. In some embodiments, the volume B532 can be a cuboid volume, a hexahedron volume, an amorphous volume or of a volume with one or more non-orthogonal sides. The peaks refer to the point where four upper faces meet and the point where four lower faces meet. The node B530 is oriented so that the horizontal vertices face the lateral sides of the cubic volume B532. The strut B531 is fixed to a lower face of the node B530 face on its proximate end and extends to the nearest corner of the cubic volume B532 at its distal end. The distal end of the strut B531 can remain fixed to the cubic volume B532 even if the node B530 changes in size to adjust the sub-unit cell properties.

On the lower face of the node B530 opposite the face which strut B531 is fixed, the proximate end of strut B534 is fixed to the node B530. The strut B534 extends to the nearest corner of cubic volume B532 at its distal end. The strut B535 is fixed on its proximate end to an upper node B530 face directed about 90 degrees laterally from the node B530 face fixed to strut B531. The strut B535 extends to the nearest corner of the cubic volume B532 at its distal end. On the upper face of the node B530 opposite the face which strut B535 is fixed, the proximate end of strut B536 is fixed to the node B530. The strut B536 extends to the nearest corner of the cubic volume B532 at its distal end.

In some embodiments, the struts B531 & B534-B536 are octahedrons with triangular faces. The strut face fixed to a node B530 face can be substantially the same size and orientation of the node B530 face. The strut face fixed to the nearest corner of the cube B532 can be substantially the same size as the strut face fixed to the node B530 and oriented on a substantially parallel plane. The remaining six faces can be six substantially similar isosceles triangles with a first internal angle and a second internal angle larger than said first internal angle. The six substantially similar isosceles triangles can be fixed along their long edges to an adjacent and inverted substantially similar isosceles triangle to form a generally cylindrical shape with triangular ends.

When forming a sub-unit cell B540, it can be beneficial to add an eighth node B538 to each corner of the cube B532 fixed to a strut B531 & B534-B536. When replicating the sub-unit cell B540, the eighth node B538 attached to each strut end is combined with eighth nodes from adjacent sub-unit cells to form nodes located between the struts of adjacent sub-unit cells.

In FIG. 1P is a first sub-unit cell B540 fixed to a second sub-unit cell B640 to form a quarter unit cell B560 used in some embodiments. The second sub-unit cell B640 comprises a square bipyramid node B630 is a square bipyramid, oriented so that the two peaks face the top and bottom of a cubic volume. The node B630 is oriented so that the horizontal vertices face the lateral sides of the cubic volume. The strut B635 is fixed to a lower face of the node B630 face on its proximate end and extends to the nearest corner of the cubic volume at its distal end. On the lower face of the node B630 opposite the face which strut B635 is fixed, the proximate end of strut B636 is fixed to the node B630. The strut B636 extends to the nearest corner of cubic volume at its distal end. The strut B634 is fixed on its proximate end to an upper node B630 face directed about 90 degrees laterally from the node B630 face fixed to strut B635. The strut B634 extends to the nearest corner of the cubic volume at its distal end. On the upper face of the node B630 opposite the face which strut B634 is fixed, the proximate end of strut B631 is fixed to the node B630. The strut B631 extends to the nearest corner of the cubic volume at its distal end.

The first sub-unit B540 is used as the datum point in the embodiment of FIG. 1P, however, it is appreciated that the second sub-unit cell B640 or another point could also be used as the datum point. Once the first sub-unit cell B540 is fixed in position, it is replicated so that the second sub-unit cell B640 is substantially similar to the first. The second sub-unit cell B640 is rotated about its central axis prior to being fixed on the top of the first unit-cell B540. In FIG. 1P, the second sub-unit cell B640 is inverted to achieve the proper rotation, however, other rotations about the central axis can achieve the same result. The first sub-unit cell B540 fixed to the second sub-unit cell B640 forms a quarter unit cell B560 that can be replicated and attached laterally to other quarter unit cells to form a full unit cell.

Alternatively, a full unit cell can be built up by fixing a first group of four substantially similar sub-unit cells together laterally to form a square, rectangle or quadrilateral when viewed from above. A second group of four substantially similar sub-unit cells rotated about their central axis can be fixed together laterally to also form a square, rectangle or quadrilateral when viewed from above. The second group of sub-unit cells can be rotated about their central axis prior to being fixed together laterally or inverted after being fixed together to achieve the same result. The second group is then fixed to the top of the first group to form a full unit cell.

In FIG. 1Q is an example of a full unit cell B770 formed by replicating the sub-unit cell B540 of FIG. 1O. The cube B532 defining the bounds of the sub-unit cell B540 is identified as well as the node B530 and struts B531 & B534-B536 for clarity. The full unit cell B770 of FIG. 1Q can be formed using the methods described above or using variations within the inventive concept.

Each strut extending from the node, for a given unit cell, can be substantially the same length and angle from the horizontal plane, extending radially from the node. At the end of each strut, the strut is mirrored so that struts extending from adjacent node faces form a rhombus shaped opening. Because the struts can be non-orthogonal to the node faces, rhombuses of two shapes emerge. In this configuration, a first group of four rhombuses extend radially from the node oriented in vertical planes. The acute angles of the first group of rhombuses equal twice the strut angle from the horizontal plane and the obtuse angles equal 180 less the acute angles. Also in this configuration is a second group of eight rhombuses extending radially so that a portion of the second group of eight rhombuses fall within the lateral separation angle between adjacent struts defining the first group of four rhombuses. The acute angles of the second group of rhombuses can be about the same as the lateral separation angle between adjacent struts that define the first group of four rhombuses and the obtuse angles equal 180 less the acute angles. The characteristics of a scaffold may also be described by its surface area per volume. For a 1.0 mm×1.0 mm×1.0 mm solid cube, its surface area is 6.0 square mm. When a 1.0 cubic mm structure is comprised of a lattice structure rather than a 100 percent volumetric density material, the surface area per volume can increase significantly. In low volumetric density scaffolds, the surface area per volume increases as the volumetric density increases. In some embodiments, a scaffold with a volumetric density of 30.1 percent would have a surface area of 27.4 square mm per cubic mm. In some embodiments, if the volumetric density was decreased to 27.0 percent, the lattice would have a surface area of 26.0 square mm per cubic mm and if the volumetric density were decreased to 24.0 percent, the lattice would have a surface area of 24.6 square mm per cubic mm.

The MRDD and RDDR structures disclosed herein also have the advantage of an especially high modulus of elasticity for a given volumetric density. When used as a lattice or scaffold, an implant with an adequate modulus of elasticity and a low volumetric density can be achieved. A low volumetric density increases the volume of the implant available for bone ingrowth.

In Table 1, below, are a number of example lattice configurations of various lattice design elastic moduli. An approximate actual elastic modulus was given for each example, representing a calculated elastic modulus for that lattice after going through the manufacturing process. The lattice structures and implants disclosed herein can be designed to a design elastic modulus in some embodiments and to an approximate actual elastic modulus in other embodiments. One advantage of the presently disclosed lattice structures is that the approximate actual elastic modulus is much closer to the design elastic modulus than has been previously achieved. During testing, one embodiment of a lattice was designed for a 4.0 GPa design elastic modulus. Under testing, the lattice had an actual elastic modulus of 3.1 GPa, achieving an actual elastic modulus within 77 percent of the design elastic modulus.

For each lattice design elastic modulus, a volumetric density, ratio of design elastic modulus to volumetric density, surface area in mm², ratio of surface area to volumetric density and ratio of surface area to lattice design elastic modulus is given.

In some of the embodiments disclosed herein, the required strut thickness can be calculated from the desired modulus of elasticity. Using the following equation, the strut thickness required to achieve a particular elastic modulus can be calculated for some MRDD and RDDR structures:

Strut Thickness=$(-0.0035*(E^2))+(0.0696*E)+0.4603$

In the above equation, "E" is the modulus of elasticity. The modulus of elasticity can be selected to determine the required strut thickness required to achieve that value or it can be calculated using a preselected strut thickness. The strut thickness is expressed in mm and represents the diameter of the strut. The strut thickness may be calculated using a preselected modulus of elasticity or selected to determine the modulus of elasticity for a preselected strut thickness.

In some embodiments, the unit cell can be elongated in one or more directions to provide a lattice with anisotropic properties. When a unit cell is elongated, it generally reduces the elastic modulus in a direction normal to the direction of the elongation. The elastic modulus in the direction of the elongation is increased. It is desirable to elongate cells in the direction normal to the direction of new bone growth contained within the interconnections, openings and central voids (if any). By elongating the cells in a direction normal to the desired direction of reduced elastic modulus, the shear strength in the direction of the elongation may be increased, providing a desirable set of qualities when designing a structural scaffold. Covarying the overall stiffness of the scaffold may augment or diminish this effect, allowing variation in one or more directions.

In some embodiments, the sub-unit cells may be designing by controlling the height of the node relative to the height of the volume that defines the sub-unit cell. Controlling the height of the node can impact the final characteristics and appearance of the lattice structure. In general, increasing the height of the node increases the strut thickness, increases the volumetric density, increases the strength and increases the elastic modulus of the resulting lattice. When increasing the height of the node, the width of the node can be held constant in some embodiments or varied in other embodiments.

In some embodiments, the sub-unit cells may be designing by controlling the volume of the node relative to the volume that defines the sub-unit cell. Controlling the volume of the node can impact the final characteristics and appearance of the lattice structure. In general, increasing the volume of the node increases the strut thickness, increases the volumetric density, increases the strength and increases

TABLE 1

Table of example lattice structures based on lattice design elastic modulus in GPa

| Lattice Design Elastic Modulus (GPa) | Approx. Actual Elastic Modulus (GPa) | Volumetric Density (percent) | Ratio of Design Elastic Modulus to Volumetric Density | Surface Area (mm²) | Ratio of Surface Area to Volumetric Density | Ratio of Surface Area to Lattice Design Elastic Modulus |
|---|---|---|---|---|---|---|
| 0.3 | 0.233 | 18.5 | 1.6 | 22.5 | 121.5 | 74.9 |
| 3 | 2.33 | 29.9 | 10.0 | 27.5 | 92.2 | 9.2 |
| 4 | 3.10 | 33.4 | 12.0 | 28.8 | 86.4 | 7.2 |
| 5 | 3.88 | 36.4 | 13.8 | 29.9 | 82.2 | 6.0 |
| 6 | 4.65 | 38.8 | 15.5 | 30.7 | 79.1 | 5.1 |
| 7 | 5.43 | 40.8 | 17.2 | 31.3 | 76.9 | 4.5 |
| 8 | 6.20 | 42.1 | 19.0 | 31.8 | 75.4 | 4.0 |
| 9 | 6.98 | 43.2 | 20.8 | 32.1 | 74.3 | 4.0 | the elastic modulus of the resulting lattice. When increasing the volume of the node, the width or height of the node could be held constant in some embodiments.

In Table 2, below, are a number of example lattice configurations of various lattice design elastic moduli. An approximate actual elastic modulus was given for each example, representing a calculated elastic modulus for that lattice after going through the manufacturing process. The lattice structures and implants disclosed herein can be designed to a design elastic modulus in some embodiments and to an approximate actual elastic modulus in some embodiments. For each lattice design elastic modulus, a lattice approximate elastic modulus, a node height, a volumetric density, a node volume, a ratio of node height to volumetric density, a ratio of node height to lattice design elastic modulus and a ratio of volumetric density to node volume is given.

TABLE 2

Table of example lattice structures based on lattice design elastic modulus in GPa

| Lattice Design Elastic Modulus (GPa) | Lattice Approx. Actual Elastic Modulus (GPa) | Node Height (mm) | Volumetric Density (percent) | Node Volume (mm3) | Ratio of Node Height to Vol. Density | Ratio of Node Height to Lattice Design Elastic Modulus | Ratio of Vol. Density to Node Volume |
|---|---|---|---|---|---|---|---|
| 0.30 | 0.23 | 0.481 | 18.5 | 0.0185 | 2.60 | 1.60 | 9.98 |
| 3.00 | 2.33 | 0.638 | 29.9 | 0.0432 | 2.14 | 0.21 | 6.91 |
| 4.00 | 3.10 | 0.683 | 33.4 | 0.0530 | 2.05 | 0.17 | 6.29 |
| 5.00 | 3.88 | 0.721 | 36.4 | 0.0624 | 1.98 | 0.14 | 5.82 |
| 6.00 | 4.65 | 0.752 | 38.8 | 0.0709 | 1.94 | 0.13 | 5.48 |
| 7.00 | 5.43 | 0.776 | 40.8 | 0.0779 | 1.90 | 0.11 | 5.23 |
| 8.00 | 6.20 | 0.793 | 42.1 | 0.0831 | 1.88 | 0.10 | 5.07 |
| 9.00 | 6.98 | 0.807 | 43.2 | 0.0877 | 1.87 | 0.09 | 4.93 |

Some embodiments of the disclosed lattice structures are particularly useful when provided within an elastic modulus range between an including 0.375 GPa to 4 GPa. Some embodiments, more preferably, include a lattice structure with an elastic modulus between and including 2.5 GPa to 4 GPa. Some embodiments include a lattice structure with a volumetric density between and including five percent to 40 percent. Some embodiments, more preferably, include a lattice structure with a volumetric density between and including 30 percent to 38 percent.

The lattice structures disclosed herein have particularly robust loading and fatigue characteristics for low volumetric density ranges and low elastic moduli ranges. Some embodiments of the lattice structures have a shear yield load and a compressive yield load between and including 300 to 15000N in static and dynamic loading up to 5,000,000 cycles at 5 Hz. Some embodiments have a compressive shear strength and an axial load between and including 300 to 15000N in static and dynamic loading up to 5,000,000 cycles at 5 Hz. Some embodiments have a shear strength and an axial load between and including 300 to 15000N in static and dynamic loading up to 5,000,000 cycles at 5 Hz. Some embodiments have a torsional yield load up to 15 Nm.

In one example, the inventive lattice structure has a volumetric density of between and including 32 percent to 38 percent, an elastic modulus between and including 2.5 GPa to 4 GPa and a shear strength and an axial load between and including 300 to 15000N in static and dynamic loading up to 5,000,000 cycles at 5 Hz. Some examples include a first set of substantially homogeneous openings with a width of about 200 μm to 900 μm and a second set of substantially homogenous openings with a width of about 1 to 15 times the width of the first set of openings, where the number of openings in the second set are provided at a ratio of about 1:8 to 1:12 relative to the number of openings in the first set.

The disclosed structures can also have benefits when used in applications where osteointegration is not sought or undesirable. By including a growth inhibiting coating or skin on a structure, the lattice disclosed herein can be used to provide structural support without providing a scaffold for bone growth. This may be desirable when used in temporary implants or medical devices that are intended to be removed after a period of time.

The present invention includes a fluid interface system for use in medical implants. The fluid interface system described herein can include at least one or more fluid interface channels disposed within an implant. The fluid interface system optionally includes fluid redirection channels, fluid interface ports and a corresponding instrument to direct fluid into the fluid interface ports. While the exemplary embodiments disclosed herein can comprise a lattice, the disclosed invention may be adapted for use in a nonporous, largely nonporous or partially nonporous implant. Only exemplary embodiments are shown herein, and it is understood that the component parts of the fluid interface system could be changed or optimized for different types of fluid within the inventive concept expressed herein.

In 1R is a first exemplary embodiment of a fluid interface system (hereinafter "interface system") adapted for use on an implant 10. In 1R, the implant 10 is shown from the top and has been sectioned horizontally through its vertical center. 1R also includes line A to show the location of some later disclosed sectioned views. Line A is nonorthogonal and traverses the left fluid interface channel 31 to show the internal structure of the fluid interface channels in various embodiments.

The implant 10 is comprises a rear portion 11 and a forward portion 12. The rear portion 11 may include a tool engagement area with a relatively high volumetric density with respect to the body 13, however, in some embodiments, it may comprise a lattice with a reduced volumetric density. The forward portion 12 may be comprise a scaffold with a reduced volumetric density, however in some embodiments, it may comprise a substantially solid material with a high volumetric density.

For clarity and ease of understanding, directions within the figures are described as front, back, right side, left side, top and bottom. The top and bottom of the implants could correspond to the superior and inferior directions, respectively, if implanted in a human spine. The term front could refer to the leading edge of the implant when being inserted during implantation. The term back refers to the end opposite the front. The term right side refers to the right side of the implant when viewed from above and the term left side refers to the side opposite the right side. These specific directional references are exemplary and used to describe the example orientations described herein.

The forward portion 12 of the implant 10 is further comprised of three distinct elongated portions—a left arm 13, a center arm 14 and a right arm 15 fixed to the rear portion 11 on one end and a front arm 16 on their distal end. The structure of the implant 10 defines a left lumen 17 and a right lumen 18 where the left lumen 17 is defined laterally by the left arm 13, center arm 14, rear portion 11 and front arm 16 and the right lumen is defined laterally by the center arm 14, right arm 15, rear portion 11 and front arm 16. In the implant 10, the left arm 13, center arm 14, right arm 15 and front arm 16 are comprised of a single material, but they could alternatively be separate segments that are later attached. In some embodiments, the arms 13-16 comprise a structural scaffold with uniform isotropic properties, a structural scaffold with ununiform isotropic properties, a structural scaffold with uniform anisotropic properties and/or a structural scaffold with ununiform anisotropic properties. In some embodiments, the rear portion 11 and the forward portion 12 are comprised of the same material but with a different volumetric density. In some embodiments, lumen 17 & 18 may be entirely distinct or may be contiguous out-of-plane.

In the implant 10, fluid can enter the interface system through one of the three fluid interface ports located on the back of the implant 10. When comprised, at least in part, of an open cell structure, fluid can enter the implant 10 through any exterior surface. The back portion 11 is comprised of a left fluid interface port 21, a center fluid interface port 22 and a right fluid interface port 23. Three fluid interface ports 21-23 are shown in the first exemplary embodiment of the interface system, however the number of fluid interface ports may be increased or decreased based on the size of the implant 10 and the configuration of the interface system. As few as a single fluid interface port may be used to transport fluid within an implant and many more fluid interface ports may be used in larger implants or where a low viscosity fluid is transported over an area. In some embodiments, no fluid interface ports are provided. In embodiments without fluid interface ports, fluid may be transferred in or out of the implant volume through methods including but not limited to capillary action or dispersion. In some embodiments, the fluid interface ports 21-23 can be free floating on a portion of the implant 10.

In the implant 10, the fluid interface ports 21-23 are threaded openings that are also configured to receive a correspondingly threaded end of an insertion tool. The configuration of the fluid interface ports 21-23 in the first exemplary embodiment of the invention is visible in the perspective view of FIG. 15. The threads contained within the fluid interface ports 21-23 may be configured to receive the threaded end of an insertion tool, the threaded end of a fluid interface device or a tool configured to aid in the insertion or transfer of a fluid. In some embodiments, a hollow insertion tool with an unobstructed center engages the threads of the fluid interface ports 21-23 to allow manipulation of the implant while fluid communicates between a hollow area in the insertion tool and the fluid interface ports 21-23. In some embodiments, the fluid interface ports are located on the right side, front and/or left side of the implant, but do not contain threads corresponding to the threaded end of an insertion tool. In some embodiments, the fluid interface ports are located on the right side, front and/or left side of the implant, and contain threads corresponding to the threaded end of an insertion tool. In some embodiments, the inserter attachment is not threaded. In some embodiments, the fluid interface ports 21-23 are configured to attach to an insertion tool using a quarter locking mechanism using the partial rotation of a cannula to engage a pin, wedge or tip of the insertion tool. In other embodiments, a means for secure attachment is used to temporarily attach an insertion tool to one or more fluid interface port 21-23. While an insertion tool is disclosed to transfer fluid through a fluid interface port 21-23, an insertion tool configured for this purpose is not needed to insert or remove fluid from the fluid interface ports. For example, a syringe could be used to either insert or remove fluid from the fluid interface ports 21-23. Such a device may be generic or specifically designed or selected to function with the interface ports.

In some embodiments, once a fluid enters the fluid interface ports 21-23, it is distributed to various areas of the implant through fluid interface channels. In some embodiments, a fluid redirection channel 24 & 25 is needed to redirect fluid from a fluid interface port 21-23 to a fluid interface channel 31-33. The fluid redirection channels 24 & 25 are useful in applications where a fluid flow needs to turn sharply between a fluid interface port and a fluid interface channel. The implant 10 can include a left fluid redirection channel 24 and a right fluid redirection channel 25 to turn fluid between the fluid interface channels and the fluid interface ports. In the interface system of implant 10, the center fluid interface channel 32 connects to the center fluid interface port 22 without requiring a fluid to make a turn, therefore making the use of a fluid redirection channel unnecessary at the center of the implant 10.

The fluid interface systems described herein can be used to transport fluid in more than one direction, singularly or simultaneously. Fluids may be gravity fed, pulled into or out of the implant through physiological forces, etc. In some embodiments, fluid can be injected into the implant via the fluid interface ports 21-23. In some embodiments, fluid can be removed from the implant via the fluid interface ports 21-23. In some embodiments, the fluid interface ports 21-23 can provide an area for fluid to freely communicate within and outside of the implant.

The exemplary interface system in implant 10 includes a left fluid interface channel 31, center fluid interface channel 32 and right fluid interface channel 33. The fluid interface channels 31-33 provide a conduit for fluids to travel between the fluid interface ports 21-23 or fluid redirection channels 24 & 25 (if used) and the internal volume of the implant 10. In some embodiments, the fluid interface channels 31-33 comprise voids within the implant capable of transporting fluid throughout the volume of the implant or to its surfaces. In some embodiments, the fluid interface channels 31-33 are areas of lower volumetric density within a lattice that allow fluids to pass with less resistance than the bulk of the lattice structure. In some embodiments, the fluid interface channels 31-33 comprise a different material than the surrounding implant.

The fluid interface channels 31-33 may comprise an internal void as depicted in FIGS. 1-3. In some embodiments, the fluid interface channels 31-33 comprise a void of any size contained within the implant 10. In some embodiments, the fluid interface channels 31-33 comprise a void contained within a single lattice unit cell. In some embodiments, the fluid interface channels 31-33 comprise a void contained within the lattice structure. In some embodiments, the body comprises an MRDD lattice structure, where the central void of a single unit cell comprises a fluid interface channel. Any void fluidly connected to the fluid interface channel can be considered part of that fluid interface channel, a branch of that fluid interface channel or a distinct fluid interface channel. Therefore, a fluid interface channel within a lattice structure may be as small as a single void that is fluidly connected to another portion of the implant 10.

In some embodiments, the fluid interface channels 31-33 comprise a volume of reduced volumetric density in comparison to the volumetric density of another portion of the implant 10. The volumetric density of the fluid interface channels 31-33 can be modified to optimize the fluid pressure in the channel for a specific type of fluid. In some embodiments, the volumetric density of the fluid interface channels 31-33 is zero percent. In some embodiments, the volumetric density of the fluid interface channels 31-33 is greater than zero percent. In some embodiments, the volumetric density of the fluid interface channels 31-33 is less than 100 percent. In some embodiments, the volumetric density of the fluid interface channels 31-33 is less than 0.95 times the volumetric density of another portion of the implant 10. In some embodiments, the volumetric density of the fluid interface channels 31-33 is less than 0.75 times the volumetric density of another portion of the implant 10. In some embodiments, the volumetric density of the fluid interface channels 31-33 is between and including zero and 0.6 times the volumetric density of another portion of the implant 10.

The fluid interface channels 31-33 may be optimized for the viscosity and surface tension of a particular fluid by varying the parameters of the fluid interface channels. The parameters of the fluid interface channels 31-33 include, but are not limited to, the diameter, the permeability of the channel walls, the permeability or density of the channels, the density of the material injected into the channel, surface tension between the device and fluid, and the viscosity of the fluid injected into the channel. For example, a fluid with higher viscosity could optimally use a larger diameter channel, higher wall permeability and/or lower channel density as compared to a fluid with a lower viscosity. In some embodiments intended for low viscosity fluids, the fluid interface channels 31-33 are regions of reduced density to increase the surface area of the fluid interface channels, increasing the wicking effect towards the exterior surfaces of the implant. In some embodiments intended for low viscosity fluids, the fluid interface channels 31-33 are regions of reduced density to increase the surface area and create comparatively negative pressure of the fluid interface channels, increasing the wicking effect and influx of fluid from the exterior surfaces of the implant.

While some potential parameters of the fluid interface channels have been given, other parameters or variables are also applicable, and they may be changed singularly or multiply. For example, a fluid interface channel 31-33 may only use a varying diameter to achieve its optimization goal or a fluid interface channel may use a varying diameter and a varying wall permeability to achieve its optimization goal.

When using the fluid interface system of the present invention in an implant comprised in part or in whole of a lattice, the fluid interface channels 31-33 do not necessarily have to reach the surface of the implant to be effective. Lattice structures can allow a certain amount of fluid to disperse through them. In a lattice, the fluid interface channels could terminate short of the exterior of the implant and fluid could disperse through a layer of lattice between the fluid interface channels and an implant surface. When using the fluid interface system of the present invention in an implant with a solid, nonporous surface, the fluid interface channels should typically terminate at the surface of the implant.

The fluid interface channels 31 & 33 may also be configured to preferentially transport fluid towards or away from a particular location in the implant 10. The tendency of the fluid interface channels 31 & 33 to preferentially transport fluid can be accomplished by using the fluid interface channel parameters to either increase or decrease fluid pressure in areas of the fluid interface channels or the implant to create a fluid pressure differential. A fluid pressure differential can be used to move fluid towards the lower pressure area and can be accomplished in response to a designed fluid pressure differential or an externally applied fluid pressure differential. An externally applied fluid pressure differential can be applied to an implant by allowing fluid, with a higher or lower fluid pressure than the fluid internal to the implant, to communicate with the fluid interface ports 21-23.

In some embodiments, the fluid interface channels 31 & 33 can be configured to preferentially deliver fluid to the lumen 17 & 18 prior to the delivery of fluid through the exterior sides of the implant 10. In some embodiments of the interface system of the implant 10, the fluid interface channels 31 & 33 are preferentially positioned nearer to lumen 17 & 18 respectively, as compared with the outer surfaces of the implant. This bias allows excess fluid to permeate into the lumen rather than exiting the outer surfaces of the device. In some embodiments, the walls of the fluid interface channels 31 and 33 are 40% to 70% further from the external surface of the device as compared to the distance from the lumen to preferentially deliver fluid to the lumen 17 & 18. In some embodiments, the walls of the fluid interface channel 31 & 33 are 60% to 63% further from the external surface of the device as compared to the distance from the lumen. In some examples, the walls of the fluid interface channels 31 & 33 are greater than 1.0 times further from the external surface of the device compared to the distance from the lumen. In some examples, the walls of the fluid interface channels 31 & 33 are greater than 1.0 times and up to 3.0 times further from the external surface of the device compared to the distance from the graft window. In some examples, the walls of the fluid interface channels 31 & 33 are about 1.6 times further from the external surface of the device compared to the distance from the graft window. In some embodiments, the magnitude of preference will vary depending on the properties of the fluid.

In some embodiments, the positioning of the fluid interface channels 31 & 33 can be measured based on the number of lattice unit cells located between the edge of the fluid interface channel and an exterior surface, where an exterior surface can be any surface of the implant, including the lumen 17 & 18 walls. In some embodiments, the fluid interface channels 31 & 33 are located one or more unit cells from the lumen 17 & 18 walls. In some embodiments, the fluid interface channels 31 & 33 are located one or more unit cells from an exterior surface of the implant 10. In some embodiments, the fluid interface channels 31 & 33 are located one or more unit cells from a lateral exterior surface of the implant 10. In some embodiments, the fluid interface channels 31 & 33 are located one or more unit cells from an upper or lower exterior surface of the implant 10.

In some embodiments, the fluid interface channels 31 & 33 can be configured to preferentially deliver fluid to the lumen 17 & 18 prior to the delivery of fluid through the exterior sides of the implant 10 through the use of reduced wall density, increased wall permeability and/or increased channel diameter on the side of the fluid interface channel closest to a lumen. These methods may be accomplished by reducing wall density on the side of the fluid interface channel closest to a lumen wall, increasing wall permeability of the fluid interface channel wall closest to a lumen wall or increasing the fluid interface channel diameter in the area of the fluid interface channel closest to a lumen wall. These methods may be used instead of or in combination with physically placing the walls of the fluid interface channels 31 & 33 closer to the lumen 17 & 18 than the exterior walls. In some embodiments, the fluid interface channels 31 & 33 may be directly connected to their respective lumen 17 & 18, terminating in the lumen to direct fluid to the lumen prior to dispersing fluid through an exterior wall.

The location or characteristics of the fluid interface channels 31-33 may also be modified to counteract the force of gravity on the injected fluid. For example, if the implant 10 implant was expected to be implanted in its upright orientation, the fluid interface channels 31-33 could be located nearer to the upper surface of the implant or configured to preferentially deliver fluid to the upper side of the implant to counteract the expected force of gravity on the fluid. The direction of preference to counteract gravity can be selected based on various positions, including but not limited to, the position of the implant during implantation or the position of the implant post-implantation.

In some embodiments, the fluid interface channels 31 & 33 are configured to favor delivery of a fluid outside of the implant 10 rather than to the lumen 17 & 18. Fluid may be preferentially directed to the exterior of the implant 10 by physically locating the interface channels closer to the exterior than the lumen 17 & 18, reducing wall density on the side of the fluid interface channel closest to an exterior wall, increasing wall permeability of the fluid interface channel wall closest to an exterior wall and/or increasing the fluid interface channel diameter in the areas of the fluid interface channel closest to an exterior wall. While the methods of favoring fluid delivery disclosed involve taking an action to change the fluid interface channel characteristics in the direction where fluid is to be favored, the inverse action may optionally be taken. For instance, instead of increasing wall permeability in the favored direction, one could decrease wall permeability in the disfavored direction. In some embodiments, the fluid interface channels 31 & 33 may be directly connected to the outside of the implant or terminate at an exterior wall of the implant.

In FIG. 2 is a side sectioned view of the implant 10 shown from the left side and sectioned vertically through the horizontal center. The center arm 14 narrows down as it extends away from the fluid interface port 22 and the fluid interface channel 32 also narrows in that direction. The fluid interface channel 32 can narrow in the direction away from the fluid interface port 22 to maintain distance from the surface of the center arm 14 and/or to maintain constant pressure within the fluid interface channel 32. Narrowing, in reference to the fluid interface channels, means a reduction in cross-sectional area. A fluid interface channel that is narrowing in a direction has a decreasing cross-sectional area in that direction. The channel pressure and dispersion characteristics to the surface of the center arm 14 may also be changed by modifying parameters other than the distance of the channel to the surface or the diameter of the channel.

Such a channel may also be applied for transporting fluid deep into a device, such as to fill the front arm 16 or a branching channel connected to the front arm 16.

The fluid interface channels 31-33 disclosed in this and other embodiments can be configured to follow or benchmark any contour in an implant. Possible contours in an implant can include, but are not limited to, an exterior surface, a density contour, a lumen, a perforation, an internal structure or a marker. In some embodiments, the fluid interface channels 31-33 can be configured to follow or benchmark any predetermined internal shape, location or contour, whether physical or conceived.

In FIG. 3 is a side sectioned view of the implant 10 shown from the left side and sectioned vertically through line A shown in 1R. Line A crosses through the left arm 13 and the left fluid interface channel 31 to show the side profile of the fluid interface channel 31 in this embodiment. In the first exemplary embodiment, the fluid interface channel 31 is taller than wide to increase the consistency of lateral flow.

In the interface system of the implant 10, the fluid interface channels 31 & 33 can be a fixed height. Alternatively, the height of the fluid interface channels can vary to maintain a fixed spacing between a top or bottom wall of the channel and the endplates, similar to the fixed spacing of the fluid interface channel to the lumen or exterior wall disclosed above for preferential flow.

The location and configuration of the fluid interface channels in the embodiments disclosed herein are shown in a vertically sectioned view, however, they are not limited to any single plane in their shape or characteristics. The fluid interface channels are never constrained to any plane but may follow the three-dimensional volume of the implant to appropriately transport fluid as required by the implant.

In FIG. 4 is a side sectioned view of a second embodiment of the fluid interface system shown in a second implant 110. The elements in the alternative embodiments which are substantially the same as the corresponding elements of the first embodiment described are identified with the same numeral. Elements which are similar (but not necessarily identical) in function are denoted by the same numeral plus 100.

The second implant 110 in FIG. 4 is substantially the same shape as the first implant 10 on its exterior and when viewed from above, only differing in the shape of the fluid interface channels. The implant 110 is shown from the left side in FIG. 4 and sectioned vertically through a location similar to line A as shown in 1R. Because the second implant 110 is substantially the same shape as the first implant 10 when viewed from above, line A represents an accurate depiction of the section line used in FIG. 4.

The interface system, as shown in implant 110, comprises one or more fluid interface channels that spit into at least two branches. A branch, with respect to a fluid interface channel is not limited by size or direction. A branch can include any opening or void in an implant that provides a path for fluid to travel, whether it provides a conduit to a different location or terminates within the branch itself. In some embodiments, a branch comprises a single lattice unit cell open to a fluid interface channel. In some embodiments, lattice unit cells near the perimeter of a fluid interface channel are modified by removing struts to create tangential channels or branches from the center channel. Branches do not need to be constrained to a single plane and may follow the geometry or shape of the implant.

The left fluid interface channel 131 in left arm 113 is shown in FIG. 4 as an example of a branched fluid interface channel and the right side can be a mirror image or of a different design. The fluid redirection channel 124 connects the fluid interface port 121 and the left fluid interface channel 131. The left fluid interface channel 131 is taller than wide and splits into a lower branch 141 and an upper branch 142. While the second embodiment discloses a fluid interface channel 131 with a lower branch 141 and upper branch 142, in some embodiments, the fluid interface channel 131 bifurcates split. In some embodiments, the fluid interface channel 131 splits laterally into two branches positioned at a substantially equal height. In some embodiments, the fluid interface channel 131 splits into branches aligned with a plane other than the vertical or horizontal planes. In some embodiments, the fluid interface channel 131 bifurcates into branches aligned with different planes. In some embodiments, the fluid interface port 121 can be free floating on a portion of the implant 110.

In FIG. 5 is a side sectioned view of a third embodiment of the fluid interface system shown in a third implant 210. The third implant 210 in FIG. 5 is substantially the same shape as the first ALIF implant 10 on its exterior and when viewed from above, differing only in the shape of the fluid interface channels. The implant 210 is shown from the left side in FIG. 5 and sectioned vertically through a location similar to line A as shown in 1R. Because the third implant 210 is substantially the same shape as the first implant 10 when viewed from above, line A represents an accurate depiction of the section line used in FIG. 5.

The interface system, as shown in the implant 210, comprises one or more fluid interface channels with a plurality of branches. The left fluid interface channel 231 in left arm 213 is shown in FIG. 5 as an example of a fluid interface channel with a plurality of branches and the right side can be a mirror image or of a different design. The fluid redirection channel 224 connects the fluid interface port 221 and the left fluid interface channel 231. The left fluid interface channel 231 is taller than wide and splits into a plurality of branches 251 generally extending upward or downward from the center of the left fluid interface channel 231. In some embodiments, the branches 251 may extend laterally from the fluid interface channel 231 or both laterally and vertically. In some embodiments, the branches 251 can extend in any direction, including laterally, vertically, forward, rearward and any three-dimensional combination between all directions. In some embodiments, the fluid interface port 221 can be free floating on a portion of the implant 210.

In FIG. 6 is a bottom sectioned view of a fourth embodiment of the fluid interface system shown in a fourth implant 310. The fourth implant 310 in FIG. 6 is substantially the same shape as the first implant 10 on its exterior and when viewed from above, only differing in the shape of the fluid interface channels. The fourth implant 310 is shown from the bottom in FIG. 6 and sectioned horizontally at approximately 20% of its height.

The interface system, as shown in the implant 310, comprises one or more fluid interface channels with a connecting channel 361. The implant 310 has at least a left arm 313 with a left fluid interface channel 331 and a right arm 315 with a right fluid interface channel 333. The implant 310 may optionally have a center arm 314 and additional fluid interface channels. The left arm 313 and right arm 315 are connected on the rear side 319 of the implant 310. Within the rear side 319 of the implant 310 is a connecting channel 361 allowing fluid to pass from the right fluid interface channel 333 to the left fluid interface channel 331 and vice versa. The connecting channel 361 may optionally connect to a center fluid interface channel or additional fluid interface channels and/or branches.

In FIG. 7 is an isometric view of an exemplary fluid interface system included in an implant 610 where the fluid interface system contained within the implant is represented by broken lines. On the exterior of the implant 610 and extending to its interior are a left fluid interface port 621, a center fluid interface port 622 and a right fluid interface port 623. The left fluid interface port 621 is open to a left fluid redirection channel 624 and the right fluid interface port 623 is open to a right fluid redirection channel 625. The center fluid interface port 622 is open to a center fluid interface channel 632. The left fluid redirection channel 624 is open to the left fluid interface channel 631 and the right fluid redirection channel 625 is open to the right fluid interface channel 633. In some embodiments, the fluid interface ports 621-623 can be free floating on a portion of the implant 610.

In FIG. 8 is a side sectioned view of a fifth embodiment of the fluid interface system shown in an implant 470. The implant 470 is sectioned vertically through its horizontal center and is shown from the left side. The rear side of the implant 470 contains a fluid interface port 472 connected to a fluid interface channel 473. The fluid interface channel 473 extends into the body 471 of the implant 470 and fluid can travel through the body 471 comprising a lattice structure. In some embodiments, the fluid interface port 472 can be free floating on a portion of the implant 470.

In FIG. 9 is a perspective view of the first exemplary embodiment of the invention adapted for use in a first implant 10, showing the exemplary configuration of fluid interface ports 21-23 on the rear or anterior side of the implant 10. The configuration of the fluid interface ports 21-23 in FIG. 9 is one example and their position and size could be modified within the inventive concept disclosed herein. In some embodiments, the number of fluid interface ports 21-23 can be increased or decreased. In some embodiments, one or more fluid interface port 21-23 is replaced with a tool engagement area without the functionality of a fluid interface port. In some embodiments, one or more fluid interface port 21-23 is replaced with a fluid interface port without a tool engagement area.

In FIG. 10 is a side sectioned view of a sixth embodiment of the fluid interface system shown in a sixth implant 510. The sixth implant 510 in FIG. 10 is substantially the same shape as the first implant 10 when viewed on its exterior and from above, only differing in the shape and wall configuration of the fluid interface channels. The implant 510 is shown from the left side in FIG. 10 and sectioned vertically through a location similar to line A as shown in 1R. Because the sixth implant 510 is substantially the same shape as the first implant 10 when viewed from above, line A represents an accurate depiction of the section line used in FIG. 10.

The interface system shown in the implant 510 comprises one or more fluid interface channels, at least partially lined with a substantially solid wall further comprising selectively placed pores. The left fluid interface channel 531 in the left arm 513 is shown in FIG. 10 as an example of a fluid interface channel with a substantially solid wall portion further comprising selectively placed pores and the right side can be a mirror image or of a different design. The fluid redirection channel 524 connects the fluid interface port 521 and the left fluid interface channel 531. In some embodiments, the fluid interface port 521 can be free floating on a portion of the implant 510. The left fluid interface channel 531 is taller than wide and further comprises a substantially solid wall 581 portion with selectively placed pores 582. The substantially solid wall 581 portion and/or the pores 582 can cover the entire inner wall or partially cover the inner wall of the left fluid interface channel 531. The pores 582 are generally characterized as openings that allow fluid to communicate from one side of the substantially solid wall 581 to another. The pores 582 may be circular in shape or not circular in shape. If circular, the pores 582 may all be the same diameter or may be more than one diameter. A single pore 582 may also be more than one diameter (i.e. if tapered in one or more directions). If not circular, in shape, the pores 582 may all have the same opening surface area or may have more than one opening surface areas. A single pore 582 may also have more than one opening surface area.

The substantially solid wall 581 with selectively placed pores 582 allows further control of the transport of fluid. In some embodiments, the use of a substantially solid wall 581 with or without selectively placed pores 582 may be desirable on an exterior surface of the implant. The substantially solid wall(s) 581 with pores 582 of a controlled size and quantity (hereinafter "solid controlled pore walls") can be included using a variety of manufacturing techniques. For implants manufactured using an additive process, solid controlled pore walls may be added to the design and printed with the implant as it is created in the additive process. The solid controlled pore walls may comprise the same material as other portions of the implant and/or of other materials. The solid controlled pore walls may also be manufactured using a surface treatment after the implant is manufactured. For instance, a coating, such as HA, could be applied to the fluid interface channel walls or the exterior walls of an implant. HA coatings may be applied using a variety of methods, including but not limited to, dip coating, sputter coating, plasma spraying, pulsed laser deposition, hot pressing, hot isostatic pressing, electrophoretic deposition, thermal spraying and sol-gel. Depending on the method of application and the number of applications, an HA coating may be less than 0.005 micrometers thick, ranging to thickness values over 2.0 milliliters (mm). When an HA coating is applied to a lattice or scaffold, it creates a layer of a certain thickness, reducing the size of the openings or interconnections between adjacent struts in the structure. If applied to a sufficient surface thickness, an HA coating can be used to create a solid controlled pore wall after the manufacture of a lattice or scaffold. When using an HA coating to create a solid controlled pore wall from a lattice structure, the HA coating is ideally applied to a certain thickness based on the desired pore size and the size of the unit cells in the base lattice or scaffold structure. For instance, if the unit cells are 2.0 mm wide and constructed of 0.5 mm diameter struts, the central void will be about 1.0 mm wide. If a central void or pore of about 0.2 mm is desired, the HA or other coating would need to be applied to a thickness of about 0.4 mm.

When applying an HA or other surface coating in a liquid form to an exterior wall of an implant, the exterior wall may be dipped in the fluid. The implant may be dipped in the fluid multiple times to build up the coating to the desired thickness. When applying an HA or other surface coating to an interior surface of an implant, such as the fluid interface channels, the coating may be heated to a vapor and sprayed onto the desired surfaces. The coating may be reapplied as necessary to achieve the desired coating thickness.

While several examples have been described herein including different fluid channels, other examples are possible. For example, fluid channels from different exemplary embodiments can be implemented in combination with one another, where one side of an implant defines a first set of channels (e.g., from FIG. 2) and another side of the implant defines a second set of channels, which can be distinct from the first set (e.g., from FIG. 3).

In some embodiments, it may be desirable to stop the escape or intrusion of fluid completely from a fluid channel wall or exterior surface in some or all areas. To stop the distribution of a fluid, substantially solid walls without pores, openings or interconnections may be used and can be included using a variety of manufacturing techniques. For implants manufactured using an additive process, substantially solid walls may be added to the design and manufactured with the implant as it is created in the additive process. The substantially solid walls may comprise the primary material and/or another material. The substantially solid walls may also be manufactured using a surface treatment after the implant is manufactured. For instance, an HA coating could be applied to the fluid interface channel walls or the exterior walls of an implant. If applied to a sufficient surface thickness, an HA coating or another coating could be used to close any surface pores, openings or interconnections, creating a substantially solid wall. When using an HA coating to create a substantially solid wall from a lattice base structure, the HA coating is ideally applied to at least a certain thickness based on the size of the unit cells in the base lattice or scaffold structure. For a given central void size in a unit cell, an HA coating would need to be applied to a thickness of at least half of the central void width to create a substantially solid wall. For instance, if the unit cells are about 2.0 mm wide and constructed of about 0.5 mm diameter struts, the central void will be about 1.0 mm wide. If a substantially solid wall is desired, the HA or other coating would need to be applied to a thickness of at least about 0.5 mm. In some embodiments, a filler material, such as a bone putty or bone wax, can be added to a surface to create a substantially solid wall. In some embodiments, this filler material may be bioactive. In some embodiments, this filler material may be bioinert.

In some embodiments, the fluid interface system, the fluid interface channels, the fluid redirection channels and/or the fluid interface ports are configured to facilitate cell migration. In some embodiments, the fluid interface system, the fluid interface channels, the fluid redirection channels and/or the fluid interface ports are configured to facilitate cell attachment.

In some embodiments, the fluid interface system, the fluid interface channels, the fluid redirection channels and/or the fluid interface ports (collectively, a "fluid interface system surface") can have a roughness attributable to the properties of the implant material or structure. The term "rough" as used herein with regards to a surface characteristic refers to any surface irregularity, however small, that deviates from a perfectly smooth surface. In some embodiments, the roughness can be quantified by Ra, where Ra is the mean roughness or the arithmetic average of the absolute profile height deviations from the mean line. In some embodiments, the roughness can be quantified by Rq, where Rq is the root mean square roughness or root mean square average of the roughness profile ordinates. In some embodiments, the roughness can be quantified by Rz, where Rz is the mean roughness depth or the arithmetic average of singular roughness depths at consecutive sampling heights.

In some embodiments, the fluid interface system surface Ra is greater than zero. In some embodiments, the fluid interface system surface Ra is more than 1 nm. In some embodiments, the fluid interface system surface Ra is more than 1 µm. In some embodiments, the fluid interface system surface roughness has an Ra value in the nano, micro or macro scale. In some embodiments, the fluid interface system surface roughness has multiple Ra values that can fall within the nano, micro and macro scales. In some embodiments, the fluid interface system surface roughness has multiple Ra values that fall within each of the nano, micro and macro scales. In some embodiments, the fluid interface system surface roughness has multiple Ra values that fall within the micro and macro scales. In some embodiments, the fluid interface system surface roughness has multiple Ra values that fall within the nano and macro scales. In some embodiments, the fluid interface system surface roughness has multiple Ra values that fall within the nano and micro scales. As used herein, the nano scale tends to refer to a size measurable in nanometers or microns. As used herein, the micro scale tends to refer to a size measurable in microns. As used herein, the macro scale tends to refer to a size measurable in millimeters. In some cases, the surface irregularities can promote bone attachment. Surface irregularities can include projections, lumps and indentations. A rough surface could possess surface irregularities that are visible to the eye or it could possess surface irregularities that are only visible using magnification. Surface irregularities include any deviation from a substantially flat surface and can include irregularities with sharp edges, rounded edges and anything in between. It is understood that various other measures of roughness and surface topography may be used to achieve the devices and methods disclosed herein.

Some embodiments have a surface roughness, Ra, between and including 0 nm to 500 nm. Some embodiments have a surface roughness, Ra, between and including 0 nm to 50 nm. Some embodiments have a surface roughness, Ra, between and including 0 nm to 30 nm. Some embodiments have a surface roughness, Ra, between and including 5 nm to 10 nm. Some embodiments have a surface roughness, Rq, between and including 0 nm to 500 nm. Some embodiments have a surface roughness, Rq, between and including 0 nm to 50 nm. Some embodiments have a surface roughness, Rq, between and including 0 nm to 10 nm. Some embodiments have a surface roughness, Rq, between and including 30 nm to 50 nm. Some embodiments have a surface roughness, Rz, between and including 0 nm to 500 nm. Some embodiments have a surface roughness, Rz, between and including 0 nm to 350 nm. Some embodiments have a surface roughness, Rz between and including 0 nm to 50 nm. Some embodiments have a surface roughness, Rz, between and including 200 nm to 400 nm. In some embodiments, a fluid interface system surface has a surface energy calibrated to promote a certain property. In some embodiments, a fluid system surface has a surface energy configured to promote cell attachment. In some embodiments, a fluid system surface has a surface energy configured to promote cell migration. In some embodiments this surface energy may be attuned to multiple cell or tissue types. In some embodiments this surface energy may be configured to reduce measures of bacterial growth.

Some embodiments include a fluid interface system surface with micro-sized pores and/or nano-sized surface features. Some embodiments include localized surface features. Some embodiments include localized nano-sized surface features. Fluid interface system surfaces can be added to implants produced in an additive process through surface etching at some point during the additive process.

The fluid interface systems of the present invention have been adapted herein in exemplary implants, however, it could be adapted for use in other types of implants and other types of medical devices. In some embodiments, the implants 10, 110, 210, 310, 510 and 610 can be an Anterior Lumbar Interbody Fusion (hereinafter "ALIF") implant. In some embodiments, the implants 10, 110, 210, 310, 510 and 610 can be a cervical stand-alone implant. In some embodiments, the implants 10, 110, 210, 310, 510 and 610 can be an ankle fusion spacer implant. In some embodiments, the implant 470 can be a Posterior Lumbar Interbody Fusion (hereinafter "PLIF") implant or a Transforaminal Lumbar Interbody Fusion (hereinafter "TLIF") implant. That some exemplary embodiments comprise an ALIF, PLIF or TLIF implant does not limit the type of devices capable of using the fluid interface systems disclosed herein. A single implant can be referred to as either a PLIF or TLIF in some embodiments because it is appreciated that PLIF and TLIF implants are often very similar and sometimes indistinguishable. Compared to PLIF implants, TLIF implants may be slightly longer (front to back) and may have a curve in a lateral direction. PLIF implants are generally implanted from a straight posterior approach, where TLIF implants are generally implanted from an angle between the posterior direction and a lateral direction. Both PLIF and TLIF implants may have lordosis.

The fluid interface channels may be configured in various ways other those pictured. For instance, the fluid interface systems may include a large internal cavity, acting as a manifold to multiple fluid interface channels. While not pictured, the fluid interface system could be used on implants with a high volumetric density or closed cell design through the use of branches that extend to the exterior surface. Each channel may also connect or remain independent and include one or more baffles to direct or distribute flow. The surfaces of each fluid interface channel may be treated (acid etch, surface coating, polishing, anodization, etc.) to modify surface tension, wettability, or Reynolds number in specific regions, throughout the channel, or following gradients. Channels may be capped to prevent direct flow from the end and generate back-pressure into the channel. Channels may be positioned preferentially to take advantage of existing porosity of the device—for instance, removing nodes or struts of a repeating unit cell lattice, or preferentially utilizing voids in a repeating unit cell lattice. The exemplary embodiments of the fluid interface system disclosed herein all use an exterior fluid interface port, however, in some embodiments, the implant can be prefilled with fluid and the fluid interface port(s) omitted.

What has been described is a fluid interface system for use in medical implants. In this disclosure, there are shown and described only exemplary embodiments of the invention, but, as aforementioned, it is to be understood that the invention is capable of use in various other combinations and environments and is capable of changes or modifications within the scope of the inventive concept as expressed herein.

The invention claimed is:
1. An implant comprising:
   a body comprising a metallic lattice and defining an external surface;
   a first interface channel disposed within the implant;
   wherein the first interface channel is configured to transport a fluid;
   wherein the first interface channel comprises a volume with a first volumetric density;
   wherein another volume within the implant comprises a second volumetric density;
   wherein the first volumetric density is less than the second volumetric density; and wherein the first interface channel is configured to allow fluid communication with another location on or in the implant.

2. The implant of claim 1, wherein the first interface channel is fluidly connected to a plurality of branches.

3. The implant of claim 1, the first interface channel and branches are configured to follow a contour of the body.

4. The implant of claim 1, further comprising a repeating unit cell structure comprising a plurality of struts connected at nodes, wherein the first interface channel comprises at least the volume of a void within a single unit cell.

5. The implant of claim 4, wherein the branches further comprise at least the volume of a void within a single unit cell with shared struts along an edge of the first interface channel, defining an opening.

6. The implant of claim 1, further comprising a first fluid interface port located on the external surface and in fluid communication with the first interface channel.

7. The implant of claim 1, wherein the first interface channel has a wall portion comprising a substantially solid surface and selectively located pores extending through the wall portion.

8. The implant of claim 1, wherein the first interface channel is positioned a first distance from a first area of the external surface that is greater than 1.0 times a second distance from a second area of the external surface.

9. The implant of claim 1, wherein the first interface channel is configured to provide a pressure differential with another portion of the body or its external surface.

10. The implant of claim 1, wherein the first interface channel further comprises a surface with a mean roughness between and including 0 nm to 50 nm.

11. An implant comprising:
a body comprising an annular ring defined by a front, rear, right side and left side and a height;
wherein the body further comprises a metallic lattice;
a first interface channel disposed within the annular ring, configured to transport a fluid;
a first interface port fixed to an external surface of the annular ring and connected to the first interface channel so as to allow fluid communication between them;
wherein the first interface channel comprises a volume with a first volumetric density;
wherein another volume within the implant comprises a second volumetric density;
wherein the first volumetric density is less than the second volumetric density; and
wherein the first interface channel is configured to allow fluid communication with another location on or in the implant.

12. The implant of claim 11, wherein the annular ring has an inner wall and an outer wall, wherein the first interface channel is positioned a first distance from the inner wall and a second distance from the outer wall; and wherein the first distance is greater than the second distance.

13. The implant of claim 11, wherein the annular ring has an inner wall and an outer wall, wherein the first interface channel is positioned a first distance from the inner wall and a second distance from the outer wall; and wherein the second distance is greater than the first distance.

14. The implant of claim 11, wherein the implant further comprises a repeating unit cell structure; wherein the annular ring has an inner wall and an outer wall, wherein the first interface channel is positioned a first distance from the inner wall; wherein the first distance is measured by a number of unit cells and wherein the first distance is one or more.

15. The implant of claim 11, wherein the implant further comprises a repeating unit cell structure; wherein the annular ring has an inner wall and an outer wall, wherein the first interface channel is positioned a first distance from the outer wall; wherein the first distance is measured by a number of unit cells and wherein the first distance is one or more.

16. The implant of claim 11, further comprising a transverse arm fixed between the front and rear of the annular ring.

17. The implant of claim 11, further comprising:
a second interface channel disposed within the transverse arm;
wherein the second interface channel comprises a volume with a third volumetric density;
wherein the third volumetric density is less than the second volumetric density;
wherein the second interface channel is configured to allow fluid communication with another location within the implant; and
wherein the second interface channel follows an external contour of the transverse arm.

18. The implant of claim 11, wherein the volumetric density of the first interface channel increases in a radial direction.

19. The implant of claim 11, wherein the first interface channel is further configured to promote cell migration.

20. The implant of claim 11, wherein the first interface channel is further configured to promote cell attachment.

* * * * *